US011136408B2

(12) United States Patent
Ekimova et al.

(10) Patent No.: US 11,136,408 B2
(45) Date of Patent: Oct. 5, 2021

(54) ANTI-PD-1 ANTIBODIES, METHOD FOR PRODUCING SAME AND METHOD FOR USING SAME

(71) Applicant: JOINT STOCK COMPANY "BIOCAD", St.Petersburg (RU)

(72) Inventors: Viktoriia Mikhailovna Ekimova, Tyumen (RU); Dmitry Valeryevich Korzhavin, St.Petersburg (RU); Yulia Sergeevna Chernykh, Solikamsk (RU); Timofey Aleksandrovich Nemankin, St.Petersburg (RU); Valery Vladimirovich Solovyev, Pushchino (RU); Anna Konstantinovna Vladimirova, St.Petersburg (RU); Irina Andreevna Bulankina, Vsevolozhsk (RU); Sergei Vasilyevich Diduk, Klimovsk (RU); Olga Vladimirovna Goncharova; Anna Vladimirovna Eroshova, Bohan (RU); Iakov Lurevich Ustiugov, Berezniki (RU); Marina Vladimirovna Artiukhova, Tula (RU); Andrei Borisovich Ulitin, Puschino (RU); Roman Alekseevich Ivanov, Moscow (RU); Dmitry Valentinovich Morozov, Moscow (RU)

(*) Notice: Subject to any disclaimer, the term of this patent is extended or adjusted under 35 U.S.C. 154(b) by 0 days.

(21) Appl. No.: 16/095,800

(22) PCT Filed: Jul. 4, 2017

(86) PCT No.: PCT/RU2017/050056
§ 371 (c)(1),
(2) Date: Oct. 23, 2018

(87) PCT Pub. No.: WO2018/013017
PCT Pub. Date: Jan. 18, 2018

(65) Prior Publication Data
US 2019/0127478 A1    May 2, 2019

(30) Foreign Application Priority Data

Jul. 13, 2016  (RU) ............................ RU2016128487

(51) Int. Cl.
*A61K 39/00* (2006.01)
*C07K 16/28* (2006.01)
*C12N 15/63* (2006.01)
*A61K 39/395* (2006.01)
*A61P 31/00* (2006.01)
*A61P 35/00* (2006.01)

(52) U.S. Cl.
CPC ........ *C07K 16/2896* (2013.01); *A61K 39/395* (2013.01); *A61P 31/00* (2018.01); *A61P 35/00* (2018.01); *C07K 16/28* (2013.01); *C12N 15/63* (2013.01); *C07K 2317/31* (2013.01); *C07K 2317/732* (2013.01); *C07K 2317/734* (2013.01); *C07K 2317/92* (2013.01)

(58) Field of Classification Search
CPC .......................... C07K 16/2896; C07K 16/28; C07K 2317/24; A61P 35/00; A61K 2039/505
See application file for complete search history.

(56) References Cited

U.S. PATENT DOCUMENTS

| 2016/0052990 | A1 | 2/2016 | Ring et al. |
| 2016/0131646 | A1 | 5/2016 | Mozaffarian et al. |
| 2016/0159905 | A1 | 6/2016 | Abdiche et al. |
| 2017/0240635 | A1 | 8/2017 | Wang et al. |

FOREIGN PATENT DOCUMENTS

WO    2016/068801 A1    5/2016

OTHER PUBLICATIONS

Paul, Fundamental Immunology, 3rd Edition, 1993, pp. 292-295 (Year: 1993).*
Rudikoff et al(Proc. Natl. Acad. Sci. USA 1982 vol. 79: p. 1979). (Year: 1979).*
Pascalis et al (The Journal of Immunology (2002) 169, 3076-3084) (Year: 2002).*
Casset et al. (2003) BBRC 307, 198-205, (Year: 2003).*
Brown et al (J. Immunol. May 1996; 156(9):3285-3291 (Year: 1996).*
Vajdos et al (J. Mol. Biol., Jul. 5, 2002;320(2); 415-428) (Year: 2002).*
George et al. (Circulation. 1998; 97: 900-906), (Year: 1998).*
Brand et al., Anticancer Res. 2006; 26:463-70 (Year: 2006).*
Strome et al., The Oncologist, 2007; 12:1084-95 (Year: 2007).*
BIOCAD Sep. 29, 2014 (Year: 2014).*
Deutscher, Guide to Protein Purification p. 738 (1990). (Year: 1990).*
PCT/RU2017/050056 ISR (2017).
PCT/RU2017/050056 written opinion (2017).

* cited by examiner

*Primary Examiner* — Sheela J. Huff
(74) *Attorney, Agent, or Firm* — Anglehart et al.

(57) ABSTRACT

The present invention relates to biotechnology and comprises isolated monoclonal antibodies, in particular human monoclonal antibodies, which specifically bind to PD-1 with high affinity. The antibodies according to the invention may be chimeric, humanized or human antibodies, or antigen-binding fragments thereof, and may be used as a medicinal agent in oncology and immuno-oncology, for treating diseases associated with various cell proliferation or development disorders. The invention also relates to methods for producing said antibodies and a method for treating human diseases using said antibodies.

16 Claims, 8 Drawing Sheets
Specification includes a Sequence Listing.

M – Fermentas, unstained PW marker

| | FcRn KD, M | FcgRIa KD, M | FcgRIIIaV KD, M | FcgRIIaH KD, M | FcgRIIb KD, M |
|---|---|---|---|---|---|
| Nivolumab IgG4 | 9.52E-09±5.07E-10 | 6.40E-08±1.1E-08M | 4.20E-06±5.4E-07M | 1.60E-06±1.5E-07M | 2.80E-07±2.2E-08M |
| Pembrolizumab IgG4 | 5.10E-09±3.21E-10 | 5.00E-08±7.9E-09M | 5.00E-06±4.4E-07M | 1.30E-06±1.6E-07M | 2.30E-06±1.9E-07M |
| BCD-100 IgG1* | 9.60E-09±4.24E-10 | 7.50E-07±9.3E-08M | 7.40E-07±1.1E-07M | NA | NA |

Fig. 8

|  | Human PD1 KD, M | Cynomolgus PD1 KD, M |
|---|---|---|
| BCD-100 IgG1* | 1,86E-10 | <1.0E-12 |

SEQUENCE LISTING

```
<160> NUMBER OF SEQ ID NOS: 10

<210> SEQ ID NO 1
<211> LENGTH: 9
<212> TYPE: PRT
<213> ORGANISM: Homo sapiens
<220> FEATURE:
<223> OTHER INFORMATION: synthetic

<400> SEQUENCE: 1

Phe Thr Phe Ser Ser Tyr Trp Met Tyr
1               5

<210> SEQ ID NO 2
<211> LENGTH: 17
<212> TYPE: PRT
<213> ORGANISM: Homo sapiens
<220> FEATURE:
<223> OTHER INFORMATION: synthetic

<400> SEQUENCE: 2

Ala Ile Asp Thr Gly Gly Gly Arg Thr Tyr Tyr Ala Asp Ser Val Lys
1               5                   10                  15

Gly

<210> SEQ ID NO 3
<211> LENGTH: 23
<212> TYPE: PRT
<213> ORGANISM: Homo sapiens
<220> FEATURE:
```

```
<223> OTHER INFORMATION: synthetic

<400> SEQUENCE: 3

Cys Ala Arg Asp Glu Gly Gly Gly Thr Gly Trp Gly Val Leu Lys Asp
1               5                   10                  15
Trp Pro Tyr Gly Leu Asp Ala
            20

<210> SEQ ID NO 4
<211> LENGTH: 11
<212> TYPE: PRT
<213> ORGANISM: Homo sapiens
<220> FEATURE:
<223> OTHER INFORMATION: synthetic

<400> SEQUENCE: 4

Gly Gly Asn Asn Ile Gly Ser Lys Asn Val His
1               5                   10

<210> SEQ ID NO 5
<211> LENGTH: 7
<212> TYPE: PRT
<213> ORGANISM: Homo sapiens
<220> FEATURE:
<223> OTHER INFORMATION: synthetic

<400> SEQUENCE: 5

Arg Asp Ser Asn Arg Pro Ser
1               5

<210> SEQ ID NO 6
<211> LENGTH: 10
<212> TYPE: PRT
<213> ORGANISM: Homo sapiens
<220> FEATURE:
<223> OTHER INFORMATION: synthetic

<400> SEQUENCE: 6

Cys Gln Val Trp Asp Ser Ser Thr Ala Val
1               5                   10

<210> SEQ ID NO 7
<211> LENGTH: 129
<212> TYPE: PRT
<213> ORGANISM: Homo sapiens
<220> FEATURE:
<223> OTHER INFORMATION: synthetic

<400> SEQUENCE: 7

Gln Val Gln Leu Val Gln Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Trp Met Tyr Trp Val Arg Gln Val Pro Gly Lys Gly Leu Glu Trp Val
        35                  40                  45
Ser Ala Ile Asp Thr Gly Gly Gly Arg Thr Tyr Tyr Ala Asp Ser Val
    50                  55                  60
Lys Gly Arg Phe Ala Ile Ser Arg Val Asn Ala Lys Asn Thr Met Tyr
65                  70                  75                  80
Leu Gln Met Asn Ser Leu Arg Ala Glu Asp Thr Ala Val Tyr Tyr Cys
                85                  90                  95
Ala Arg Asp Glu Gly Gly Gly Thr Gly Trp Gly Val Leu Lys Asp Trp
            100                 105                 110
```

Pro Tyr Gly Leu Asp Ala Trp Gly Gln Gly Thr Leu Val Thr Val Ser
            115                 120                 125

Ser

<210> SEQ ID NO 8
<211> LENGTH: 107
<212> TYPE: PRT
<213> ORGANISM: Homo sapiens
<220> FEATURE:
<223> OTHER INFORMATION: synthetic

<400> SEQUENCE: 8

Gln Pro Val Leu Thr Gln Pro Leu Ser Val Ser Val Ala Leu Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Ile Tyr
        35                  40                  45

Arg Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Val Trp Asp Ser Ser Thr Ala Val
                85                  90                  95

Phe Gly Thr Gly Thr Lys Leu Thr Val Leu Gln
            100                 105

<210> SEQ ID NO 9
<211> LENGTH: 459
<212> TYPE: PRT
<213> ORGANISM: Homo sapiens
<220> FEATURE:
<223> OTHER INFORMATION: synthetic

<400> SEQUENCE: 9

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Val Pro Gly Lys Gly Leu Glu Trp Val
        35                  40                  45

Ser Ala Ile Asp Thr Gly Gly Gly Arg Thr Tyr Tyr Ala Asp Ser Val
    50                  55                  60

Lys Gly Arg Phe Ala Ile Ser Arg Val Asn Ala Lys Asn Thr Met Tyr
65                  70                  75                  80

Leu Gln Met Asn Ser Leu Arg Ala Glu Asp Thr Ala Val Tyr Tyr Cys
                85                  90                  95

Ala Arg Asp Glu Gly Gly Gly Thr Gly Trp Gly Val Leu Lys Asp Trp
            100                 105                 110

Pro Tyr Gly Leu Asp Ala Trp Gly Gln Gly Thr Leu Val Thr Val Ser
            115                 120                 125

Ser Ala Ser Thr Lys Gly Pro Ser Val Phe Pro Leu Ala Pro Ser Ser
    130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

-continued

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Arg Val Glu Pro Lys Ser Cys Asp Lys Thr His Thr Cys Pro Pro
225                 230                 235                 240

Cys Pro Ala Pro Glu Ala Ala Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
    290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Tyr Thr
            340                 345                 350

Leu Pro Pro Ser Arg Glu Glu Met Ala Lys Gly Gln Pro Arg Glu Pro
        355                 360                 365

Gln Val Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Lys Leu Thr Val Asp Lys Ser Arg Trp Gln Gln Gly
            420                 425                 430

Asn Val Phe Ser Cys Ser Val Met His Glu Ala Leu His Asn His Tyr
        435                 440                 445

Thr Gln Lys Ser Leu Ser Leu Ser Pro Gly Lys
    450                 455

<210> SEQ ID NO 10
<211> LENGTH: 214
<212> TYPE: PRT
<213> ORGANISM: Homo sapiens
<220> FEATURE:
<223> OTHER INFORMATION: synthetic

<400> SEQUENCE: 10

Gln Pro Val Leu Thr Gln Pro Leu Ser Val Ser Val Ala Leu Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Ile Tyr
        35                  40                  45

Arg Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

```
Asp Glu Ala Asp Tyr Tyr Cys Gln Val Trp Asp Ser Ser Thr Ala Val
                85              90              95
Phe Gly Thr Gly Thr Lys Leu Thr Val Leu Gln Arg Thr Val Ala Ala
            100             105             110
Pro Ser Val Phe Ile Phe Pro Pro Ser Asp Glu Gln Leu Lys Ser Gly
        115             120             125
Thr Ala Ser Val Val Cys Leu Leu Asn Asn Phe Tyr Pro Arg Glu Ala
        130             135             140
Lys Val Gln Trp Lys Val Asp Asn Ala Leu Gln Ser Gly Asn Ser Gln
145             150             155             160
Glu Ser Val Thr Glu Gln Asp Ser Lys Asp Ser Thr Tyr Ser Leu Ser
                165             170             175
Ser Thr Leu Thr Leu Ser Lys Ala Asp Tyr Glu Lys His Lys Val Tyr
            180             185             190
Ala Cys Glu Val Thr His Gln Gly Leu Ser Ser Pro Val Thr Lys Ser
        195             200             205
Phe Asn Arg Gly Glu Cys
210
```

ANTI-PD-1 ANTIBODIES, METHOD FOR PRODUCING SAME AND METHOD FOR USING SAME

TECHNICAL FIELD

The present disclosure relates to biotechnology and provides isolated monoclonal antibodies, in particular human monoclonal antibodies that specifically bind to high affinity PD-1. The antibodies of the disclosure can be chimeric, humanized or human antibodies, or antigen-binding fragments thereof, and can be used as a medicinal agent in oncology and immuno-oncology, and for treating diseases associated with various cell proliferation or development disorders. The disclosure also relates to methods of producing said antibodies and a method of treating human diseases with said antibodies.

BACKGROUND

Programmed death 1 (PD-1) protein is an inhibitory member of the CD28 receptor family that also includes CD28, CTLA-4, ICOS and BTLA. PD-1 is expressed on activated B cells, T cells, and myeloid cells (Agata et al., supra; Okazaki et al. (2002) Curr. Opin. Immunol. 14: 391779-82; Bennet et al. (2003) J Immunol 170:711-8). The initial members of this family, CD28 and ICOS, were detected by functional effects on increase in T cell proliferation following the addition of monoclonal antibodies (Hutloff et al. (1999) Nature 397:263-266; Hansen et al. (1980) Immunogenics 10:247-260). PD-1 was detected by screening for differential expression in apoptotic cells (Ishida et al. (1992) EMBO J 11:3887-95). Other members of this family, CTLA-4 and BTLA, were detected by screening for differential expression in cytotoxic T-lymphocytes and TH1 cells, respectively. CD28, ICOS and CTLA-4, all have an unpaired cysteine residue that allows them to homodimerize. In contrast, PD-1 is believed to exist as a monomer, lacking the unpaired cysteine residue characteristic in other CD28 family members.

PD-1 is a 55 kDa type I transmembrane protein that is part of the Ig gene superfamily (Agata et al. (1996) Int Immunol 8:765-72). PD-1 comprises a membrane proximal immunoreceptor tyrosine inhibitory motif (ITIM) and a membrane distal tyrosine-based switch motif (ITSM) (Thomas, M. L. (1995) J Exp Med 181:1953-6; Vivier, E H Daeron, M (1997) Immunol Today 18:286-91). Although structurally similar to CTLA-4, PD-1 lacks the MYPPY motif that is critical for B7-1 and B7-2 binding. It has been detected that PD-1 has two ligands, PD-L1 and PD-L2, which have been shown to negatively regulate T cell activation after binding to PD-1 (Freeman et al. (2000) J Exp Med 192:1027-34; Latchman et al. (2001) Nat Immunol 2:261-8; Carter et al. (2002) Eur J Immunol 32:634-43). Both PD-L1 and PD-L2 are B7 homologs that bind to PD-1, but do not bind to other members of the CD28 family.

One PD-1 ligand, PD-L1, is abundant in various human cancers (Dong et al. (2002) Nat. Med. 8:787-9). The interaction between PD-1 and PD-L1 leads to a reduction in the number of tumor-infiltrating lymphocytes, decrease in T cell receptor-mediated proliferation, and escape from immunological surveillance of cancer cells (Dong et al. (2003) J. Mol. Med. 81:281-7; Blank et al. (2005) Cancer Immunol. Immunother. 54:307-314; Konishi et al. (2004) Clin. Cancer Res. 10:5094-100). Immunosuppression may be reversed by inhibiting the local interaction of PD-L1 with PD-1, and this effect is additive when the interaction of PD-L2 with PD-1 is blocked (Iwai et al. (2002) Proc. Nat'l. Acad. Sci. USA 99:12293-7; Brown et al. (2003) J. Immunol. 170:1257-66).

PD-1 is an inhibitory member of the CD28 family and is expressed on activated B cells, T cells and myeloid cells (Agata et al., supra; Okazaki et al. (2002) Curr Opin Immunol 14: 391779-82; Bennett et al. (2003) J Immunol 170:711-8). PD-1-deficient animals are prone to developing various autoimmune diseases including autoimmune cardiopathy, and lupus-like syndrome comprised of arthritis and nephritis (Nishimura et al. (1999) Immunity 11:141-51; Nishimura et al. (2001) Science 291:319-22). In addition, PD-1 was found to play a role in autoimmune encephalomyelitis, systemic lupus erythematosus, graft-versus-host disease (GVHD), type I diabetes and rheumatoid arthritis (Salama et al. (2003) J Exp Med 198:71-78; Prokunina and Alarcon-Riquelme (2004) Hum Mol Genet 13:R143; Nielsen et al. (2004) Lupus 13:510). In a murine B cell tumor line, the ITSM of PD-1 was shown to be essential to block BCR-mediated Ca2+-flux and tyrosine phosphorylation of downstream effector molecules (Okazaki et al. (2001) PNAS 98:13866-71).

Today, there are a number of anti-PD-1 antibodies, such as nivolumab (BMS-936558, MDX-1106 or ONO-4538; BMS), pembrolizumab (Merck).

The prior art discloses monoclonal anti-PD-1 antibodies comprising certain amino acid sequences according to WO 2006/121168 (nivolumab, BMS), which exhibit some useful properties, such as high affinity binding to human PD-1, but no significant cross-reactivity with human CD28, CTLA-4 or ICOS. In addition, it has been shown that these antibodies modulate immune responses. Thus, the present application also describes a method for modulating immune responses using anti-PD-1 antibodies. In particular, the present disclosure provides a method for inhibiting in vivo growth of tumor cells using anti-PD-1 antibodies.

The prior art also discloses an isolated PD-1 binding protein described in WO2009/114335 (pembrolizumab, Merck) which comprises a first variable region and a second variable region. The first variable region is a heavy chain comprising various CDRs, and the second variable region is a light chain also comprising various CDRs.

Thus, it is important to develop antibodies that recognize PD-1, and methods of use of such agents.

SUMMARY

The present disclosure provides antibodies that specifically bind to PD-1 and have advantageous characteristics of functional activity, affinity, specificity, and stability in the test assays.

The present disclosure relates to human monoclonal antibodies that specifically bind to PD-1. Such antibodies can be used in the treatment of oncological and infectious diseases. The monoclonal antibodies of the present disclosure are believed to provide the best clinical response, as compared with current methods of treatment of said diseases, including treatment with antibodies.

In one aspect, the present disclosure relates to an antibody or antigen-binding fragment thereof that is capable of binding to a human PD-1 receptor and comprises an amino acid sequence that is at least 75% homologous to the sequence of SEQ ID NO: 3.

In one embodiment, the present disclosure relates to an antibody or fragment thereof which comprises the amino acid sequence of SEQ ID NO:3.

In some embodiments, the present disclosure relates to an antibody or fragment thereof which comprises the following:
- a sequence of a heavy chain variable domain that is at least 75% homologous to the sequence of SEQ ID NO:7, and
- a sequence of a light chain variable domain that is at least 75% homologous to the sequence of SEQ ID NO:8.

In one embodiment, the present disclosure relates to an antibody or fragment thereof which comprises the amino acid sequences of SEQ ID NO: 1-3.

In some embodiments, a binding fragment competes for binding or binds to the same epitope as a binding domain comprising the amino acid sequence of SEQ ID NO: 7.

In some embodiments, a binding fragment is at least 90% homologous to the amino acid sequence of SEQ ID NO: 7. In one embodiment of the disclosure, a binding domain comprises the amino acid sequence of SEQ ID NO: 7. In one embodiment of the disclosure, a binding domain can be humanized.

In some embodiments of the disclosure, an antibody or antigen-binding fragment thereof is characterized in that it relates to human IgG1, IgG2, IgG3, IgG4 isotypes.

In some embodiments, an antibody or fragment thereof has a heavy chain sequence that is at least 90% homologous to the sequence of SEQ ID NO 9.

In some embodiments, an antibody or fragment thereof has a light chain sequence that is at least 90% homologous to the sequence of SEQ ID NO:10.

In some embodiments, the Fc constant region of an antibody or fragment thereof comprises any mutations that reduce or eliminate any of the effector functions (ADCC, ADCP or CDC) as compared with the natural sequence.

In some embodiments, the Fc constant region of an antibody or fragment thereof comprises mutations that increase animal or human pharmacokinetic parameters, such as t½β (h) or Cmax (μg/ml).

In some embodiments, an antibody or antigen-binding fragment thereof have at least one of the following properties:
a) aggregation stability: the aggregate content does not increase by more than 5% of the initial content in solution at concentrations above 10 mg/ml and at storage temperature T=4° C. for more than 6 months;
b) aggregation stability: the aggregate content does not increase by more than 5% of the initial content in solution at concentrations above 10 mg/ml and with an increase in temperature to 37° C. for more than 2 weeks;
c) aggregation stability: the aggregate content does not increase by more than 5% of the initial content in solution at concentrations above 10 mg/ml and with an increase in temperature to 50° C. for more than 6 hours;
d) the dissociation constant KD of not more than $10^{-9}$ (M) when binding to human PD-1;
e) the kinetic association constant kon (1/Ms) of at least $10^5$ (1/Ms) when binding to human PD-1;
f) the kinetic dissociation constant dis (1/s) of not more than $10^{-4}$ (1/s) when binding to human PD-1.

In one aspect, the present disclosure relates to a bispecific antibody that comprises any antigen-binding fragment of an antibody as described above.

In one aspect, the present disclosure relates to an isolated nucleic acid molecule encoding an antibody or antigen-binding domain thereof according to any of claims 1-14.

In one aspect, the present disclosure relates to an expression vector that comprises any of isolated nucleic acid molecules described herein.

In one aspect, the present disclosure relates to a host cell that comprises any nucleotide sequence described herein.

In one aspect, the present disclosure relates to a method for producing a host cell that comprises transfection of a suitable stem cell with an expression vector.

In one aspect, the present disclosure relates to a method for the preparation of any antibody as described herein, comprising the production of a host cell, culturing of a host cell under conditions sufficient to produce said antibody or fragment thereof, followed by isolation and purification of the obtained antibody or active fragment thereof.

In some embodiments, the present disclosure relates to a pharmaceutical composition comprising an antibody or fragment thereof as described above, in combination with one or more pharmaceutically acceptable excipients, diluents or carriers. In some embodiments, a pharmaceutical composition is intended to be used for the treatment of oncological and infectious diseases.

In one aspect, the present disclosure relates to a method for inhibiting the biological activity of PD-1 in a subject in need of such inhibition, which comprises administering an effective amount of any antibody as described above.

In one aspect, the present disclosure relates to a method for treatment of a patient in need of such treatment, which comprises administering any antibody or antigen-binding fragment or pharmaceutical composition described herein.

BRIEF DESCRIPTION OF THE DRAWINGS

FIG. 8. Analysis of interactions of BCD-100 candidates with FcRn and Fcγ receptors on Octet RED 96.

DETAILED DESCRIPTION

Definitions and General Methods

Figure 1:
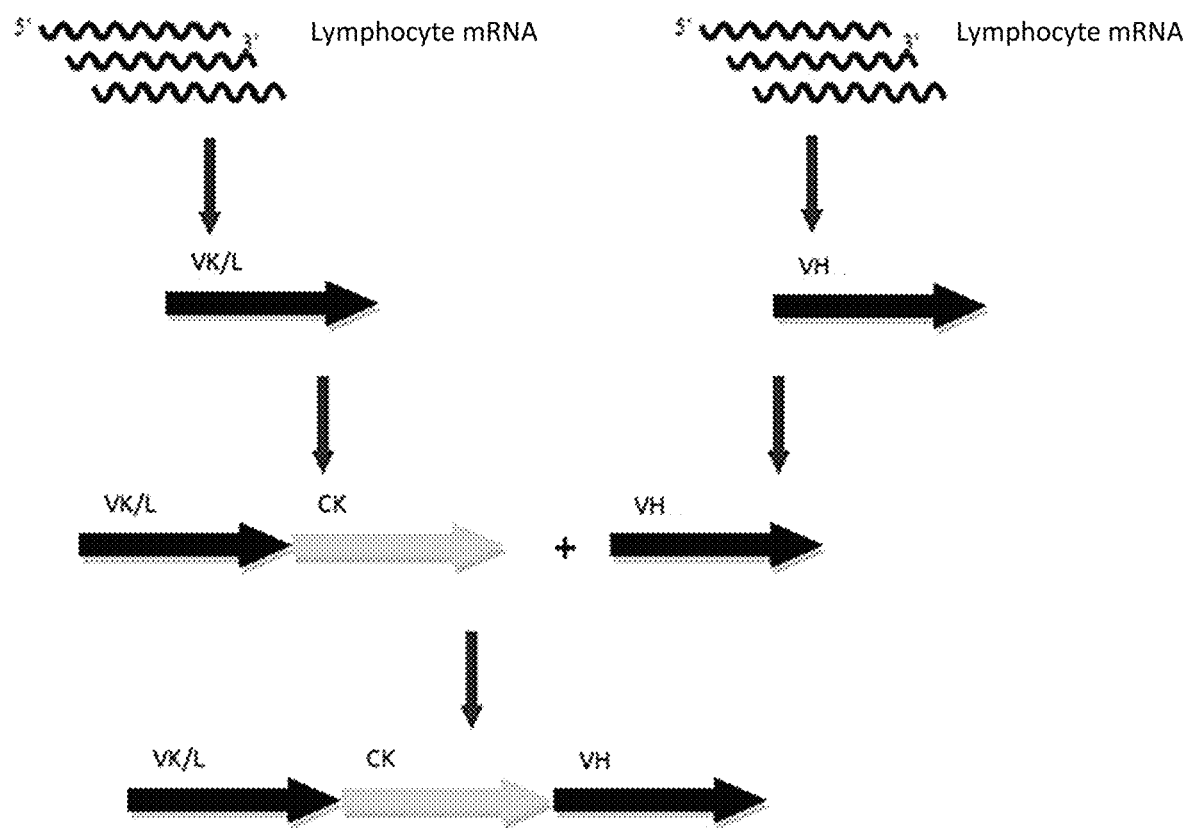
FIG. 1 Scheme of synthesis of a human naive combinatorial library.

Unless defined otherwise, all technical and scientific terms used herein have the same meaning as is commonly understood by one of ordinary skill in the art. Although methods and materials similar or equivalent to those described herein can be used in the practice or testing of embodiments of the disclosure, exemplary methods and/or materials are described below. All publications and other references mentioned herein are incorporated by reference in their entirety. In case of contradiction, this description, including definitions, shall prevail. Although a number of prior art publications are referred to herein, such references do not constitute an admission that any of these documents form part of the common general knowledge in the art.

Further, unless otherwise required by context, singular terms shall include pluralities and plural terms shall include the singular. Typically, the classification and methods of cell and tissue culture, molecular biology, immunology, microbiology, genetics, analytical chemistry, organic synthesis chemistry, medical and pharmaceutical chemistry, as well as hybridization and chemistry of protein and nucleic acids described herein are well known and widely used by those skilled in the art. Enzyme reactions and purification methods are performed according to the manufacturer's instructions, as is known in the art, or as described herein.

Throughout this disclosure and embodiments, the word "consist" and "comprise" or variations thereof, such as "consists" or "consisting", "comprises" or "comprising" shall be understood to imply the inclusion of a stated integer or group of integers but not the exclusion of any other integer or group of integers.

Definitions Related to Antibodies

As used herein, the terms "programmed death 1", "programmable cell death 1", "PD-1 protein", "PD-1", "CD279", "PDCD1", "hPD-1" and "hPD-I" are interchangeable and refer to any variants, isoforms, species homologs of human PD-1 and analogs thereof comprising at least one common epitope with PD-1.

The terms "immune response", "autoimmune response" and "autoimmune inflammation" refer, for example, to the action of lymphocytes, antigen-presenting cells, phagocytic cells, granulocytes and soluble macromolecules produced by said cells or liver cells (including antibodies, cytokines and complement produced in the result of selective damage, destruction or elimination of invasive pathogens, cells or tissues infected with pathogens, cancer cells or, in cases of autoimmunity or pathological inflammation, normal cells or tissues from the human body).

The term "binding molecule" as used herein includes antibodies, immunoglobulins and antigen-binding fragments of an antibody. The term "antibody" (Ab) or "immunoglobulin" (Ig) as used herein is intended to refer to a tetramer comprising two heavy (H) chains (about 50-70 kDa) and two light (L) chains (about 25 kDa), which are linked by disulfide bridges. Each heavy chain consists of a heavy chain variable domain (VH) and a heavy chain constant region (CH). Each light chain consists of a light chain variable domain (VL) and a light chain constant region (CL). VH and VL domains can be further subdivided into regions of hypervariability, termed "complementarity determining regions" (CDR), interspersed with regions that are more conserved, termed "framework regions" (FR). Each VH and VL is composed of three CDRs (H-CDR as used herein denotes a heavy chain CDR and L-CDR as used herein denotes a light chain CDR) and four FRs, arranged from amino-terminus to carboxy-terminus in the following order: FR1, CDR1, FR2, CDR2, FR3, CDR3, FR4. Attribution of amino acids to each region can be made in accordance with the definitions by IMGT® (Lefranc et al., Dev Comp Immunol 27(1):55-77 (2003); or the definitions by Kabat, Sequences of Proteins of Immunological Interest (National Institutes of Health, Bethesda, Md. (1987 and 1991)); Chothia & Lesk, J. Mol. Biol. 196:901-917 (1987); or Chothia et al., Nature 342:878-883 (1989).

As used herein, the terms "antibody" and "immunoglobulin" are interchangeable.

The term "antigen-binding portion" of an antibody (or "antigen portion", "fragment") as used herein is intended to refer to one or more portions or fragments of an antibody, that retain the ability to specifically bind to an antigen (e.g., PD1). It has been shown that the antigen-binding function of an antibody can be performed by some fragments of a full-length antibody. Examples of binding fragments encompassed within the term "antigen-binding portion" include (i) a Fab fragment, a monovalent fragment consisting of $V_L$, $V_H$, $C_L$ and $C_H1$ domains; (ii) a F(ab)$_2$ fragment, a bivalent fragment comprising two Fab fragments linked by a disulfide bridge at the hinge region; (iii) a Fd fragment consisting of $V_H$ and $C_H1$ domains; (iv) a Fv fragment consisting of $V_L$ and $V_H$ domains of a single arm of an antibody; (v) a single-domain antibody *dAb) fragment, which consists of a VH domain; and (vi) an isolated complementarity determining region (CDR) able to specifically bind to an antigen. Furthermore, although the two domains of the Fv fragment, $V_L$ and $V_H$, are encoded by individual genes, they can be joined, using recombinant methods, by a synthetic linker that enables them to be made as a single chain protein in which the $V_L$ and $V_H$ regions pair to form monovalent molecules (known as single chain Fv (scFv)). The present disclosure also provides antigen-binding molecules comprising V H and/or $V_L$. In the case of $V_H$, a molecule may also comprise one or more of CH1, hinge, CH2 or CH3 regions. Such single chain antibodies are also intended to be encompassed within the term "antigen-binding portion" of an antibody. Other forms of single-chain antibodies, such as diabodies, are also encompassed. Diabodies are small bivalent and bispecific antibodies, in which domain $V_H$ and domain $V_L$ are expressed on the same polypeptide chain (VH-VL). By using a linker that is too short to allow pairing between the two domains on the same chain, the domains are forced to pair with the complementary domains of another chain and create two antigen-binding sites. Antibody regions, such as Fab- and F(ab') 2 fragments can be prepared from whole antibodies using conventional techniques, e.g., papain or pepsin hydrolyses of whole antibodies. Moreover, antibodies, portions thereof and immunoadhesion molecules can be prepared using standard recombinant DNA techniques, for example, as described herein.

The term "recombinant antibody" is intended to refer to an antibody that is expressed from a cell or cell line comprising nucleotide sequence(s) encoding antibodies, wherein said nucleotide sequence(s) is not naturally associated with the cell.

As used herein, the term "variant antibody" is intended to refer to an antibody, which has an amino acid sequence that differs from the amino acid sequence of a "parental" antibody thereof by virtue of adding, deleting and/or substituting one or more amino acid residues as compared to the sequence of a parental antibody. In a preferred embodiment, a variant antibody comprises at least one or more (e.g., one to twelve, e.g., two, three, four, five, six, seven, eight or nine, ten, eleven or twelve; in some embodiments, a variant antibody comprises from one to about ten) additions, deletions, and/or substitutions of amino acids as compared to a parental antibody. In some embodiments, such additions, deletions and/or substitutions are made in the CDRs of a variant antibody. Identity or homology with respect to the sequence of a variant antibody is defined herein as the percentage of amino acid residues in the variant antibody sequence that are identical to the parental antibody residues, after aligning the sequences and introducing gaps, if necessary, to achieve the maximum percent of sequence identity. A variant antibody retains the ability to bind to the same antigen, and preferably to an epitope, to which the parental antibody binds; and in some embodiments, at least one property or biological activity is superior to that of a parental antibody. For example, a variant antibody may have, e.g., a stronger binding affinity, longer half-life, lower IC50, or enhanced ability to inhibit antigen biological activity as compared to a parental antibody. The variant antibody of particular interest herein is one which displays at least 2-fold, (preferably at least 5-fold, 10-fold or 20-fold) enhancement in biological activity as compared to a parental antibody.

In a broad sense, the term "chimeric antibody" is intended to refer to an antibody that comprises one or more regions of one antibody, and one or more regions of one or several other antibodies, typically, a partially human and partially non-human antibody, i.e. derived partially from a non-human animal, such as mice, rats, or the like vermin, or the Camelidae such as llama and alpaca. Chimeric antibodies are generally preferred over non-human antibodies in order to reduce the risk of a human anti-antibody immune response, e.g. a human anti-mouse antibody immune response in the case of a murine antibody. An example of a typical chimeric antibody is one in which the variable region sequences are murine sequences, while the constant region sequences are human. In the case of a chimeric antibody, the non-human parts may be subjected to further alteration in order to humanize the antibody.

The term "humanization" is intended to refer to the fact that when an antibody has a fully or partially non-human origin, for example, a mouse or llama antibody obtained by immunizing mice or llamas, respectively, with an antigen of interest, or is a chimeric antibody based on such an antibody of a mouse or llama, it is possible to substitute certain amino acids, in particular in the framework regions and constant domains of heavy and light chains, in order to avoid or minimize the immune response in humans. Antibodies interact with target antigens predominantly through amino acid residues that are located in the six heavy and light chains CDRs. For this reason, amino acid sequences within CDRs are far more variable between individual antibodies than those outside of CDRs. Because CDR sequences are responsible for most antibody-antigen interactions, it is possible to express recombinant antibodies that mimic the properties of a specific naturally occurring antibody, or more generally, of any specific antibody with said amino acid sequence, e.g., by constructing expression vectors that express CDR sequences from the specific antibody grafted onto framework sequences from a different antibody. As a result, it is possible to "humanize" a non-human antibody and, to a large extent, preserve binding specificity and affinity of the initial antibody. Although it is not possible to precisely predict the immunogenicity and thereby the human anti-antibody response of a particular antibody, non-human antibodies are typically more immunogenic than human antibodies. Chimeric antibodies, where the foreign (e.g. vermin or Camelidae) constant regions have been substituted with sequences of human origin, have shown to be generally less immunogenic than those of fully foreign origin, and the trend in therapeutic antibodies is towards humanized or fully human antibodies. Therefore, chimeric antibodies or other antibodies of non-human origin can be humanized to reduce the risk of a human anti-antibody response.

For chimeric antibodies, humanization typically involves modification of the framework regions of variable region sequences Amino acid residues that are part of complementarity determining regions (CDRs) will be most often not modified by virtue of humanization, although in some cases it may be desirable in order to modify individual amino acid residues of a CDR, for example, in order to delete a glycosylation site, deamidation site, aspartate isomerization site, or undesired cysteine or methionine residues. N-linked glycosylation is made by virtue of attaching an oligosaccharide chain to an asparagine residue in a tripeptide sequence Asn-X-Ser or Asn-X-Thr, where X can be any amino acid except Pro. Removal of an N-glycosylation site may be achieved by mutating either the Asn or Ser/Thr residue by a different residue, preferably by way of conservative substitution. Deamidation of asparagine and glutamine residues can occur depending on such factors as pH and surface exposure. Asparagine residues are especially susceptible to deamidation, primarily when present in sequence Asn Gly, and in a lesser degree in other dipeptide sequences such as Asn-Ala. Provided a CDR sequence comprises such a deamidation site, in particular Asn-Gly, it may be desirable to remove this site, typically by virtue of conservative substitution to delete one of the implicated residues.

Numerous methods for humanizing an antibody sequence are known in the art; see, for example, a review by Almagro & Fransson, Front Biosci. 13:1619-1633 (2008). One commonly used method is CDR grafting, when, e.g., murine chimeric antibodies involve identification of human germline gene counterparts to the murine variable region genes and grafting of the murine CDR sequences into this framework. CDR grafting may be based on the CDR definitions by Kabat, although the last edition (Magdelaine-Beuzelin et al., Crit Rev.Oncol Hematol. 64:210 225 (2007)) suggests that the IMGT® (the international ImMunoGeneTics information System®) definition may improve humanization results (see Lefranc et al., Dev. Comp Immunol. 27:55-77 (2003)). In some cases, CDR grafting may reduce the binding specificity and affinity, and thus the biological activity, of a CDR grafted non-human antibody, as compared to a parental antibody from which the CDRs were obtained. Back mutations (which are sometimes referred to as "framework region repair" may be introduced at selected positions of a CDR grafted antibody, typically in framework regions, in order to restore the binding specificity and affinity of a parental antibody). Identification of positions for possible back mutations can be performed using information available in the literature and in antibody databases. Amino acid residues that are candidates for back mutations are typically those that are located at the surface of an antibody molecule, whereas residues that are buried or that have a low degree of surface exposure will not normally be altered. An alternative humanization technique to CDR grafting and back mutation is resurfacing, in which non-surface exposed residues of non-human origin are retained, whereas surface residues are altered to human residues.

In certain cases, it may also be desirable to alter one or more CDR amino acid residues in order to improve binding affinity to the target epitope. This is known as "affinity maturation" and may optionally be performed in connection with humanization, for example in situations where humanization of an antibody leads to reduced binding specificity or affinity and it is not possible to sufficiently improve the binding specificity or affinity by back mutations alone. Various affinity maturation methods are known in the art, for example the in vitro scanning saturation mutagenesis method described by Burks et al., Proc Natl Acad Sci USA, 94:412-417 (1997) and the stepwise in vitro affinity maturation method by Wu et al., Proc Natl Acad Sci USA 95:6037 6042 (1998).

The term "isolated protein", "isolated polypeptide" or "isolated antibody" is intended to refer to a protein, polypeptide or antibody, that by virtue of origin or source of derivation thereof (1) is not associated with naturally associated components that accompany them in a native state thereof, (2) is free of other proteins from the same species, (3) is expressed by a cell from a different species, or (4) does not occur in nature. Thus, a polypeptide that is chemically synthesized or synthesized in a cellular system different from the cell from which it naturally originates will be "isolated" from its naturally associated components. A protein may also be substantially free of naturally associated components by virtue of isolation, using protein purification techniques well known in the art.

As used herein, the term "germinal" is intended to refer to the nucleotide and amino acid sequences of antibody genes and gene segments and how they are transmitted from parents to progeny via germinal cells. Germ-line sequences differ from the nucleotide sequences encoding antibodies in mature B cells that have been altered as a result of recombination and supermutation during the maturation of B cells. An antibody that "utilizes" a particular germ-line sequence has nucleotide and amino acid sequences that are aligned to a germ-line nucleotide sequence or amino acid sequence, to which it corresponds more fully than to any other germ-line nucleotide or amino acid sequences.

The term "affinity" is intended to refer to measuring the attraction between an antigen and binding molecule, e.g., an antibody. The intrinsic ability to attract a binding molecule for an antigen is typically expressed as the binding affinity equilibrium constant (KD) of a particular binding molecule-antigen interaction. A binding molecule is said to specifically bind to an antigen when KD is <1 mM, preferably <100 nM. A KD binding affinity constant can be measured, e.g., by surface plasmon resonance (BIAcore™) or bio-layer interferometry, for example using ProteOn™ XPR36 SPR (Bio-Rad) or Octet™ systems.

The term "Ka" as used herein is intended to refer to the association rate of a particular antibody-antigen interaction, whereas the term "Kd" is intended to refer to the dissociation rate of a particular antibody-antigen interaction. The term "Kd" as used herein is intended to refer to the dissociation constant, which is obtained from the ratio of Kd to Ka (i.e. Kd/Ka) and is expressed as a molar concentration (M). Kd values for antibodies can be determined using methods well established in the art.

A preferred method for determining the Kd of an antibody is surface plasmon resonance using a biosensor system such as a BIAcore™ system.

As used herein, the term "high affinity" for an IgG antibody is intended to refer to an antibody having Kd $10^{-8}$ M, more preferably $10^{-9}$ M or less and even more preferably $10^{-10}$ M or less for a target antigen. However, "high affinity" binding can vary for other antigen isotypes. For example, "high affinity" binding for an IgM isotype is intended to refer to an antibody having KD $10^{-7}$ M or less, more preferably $10^{-8}$ M or less, even more preferably $10^{-9}$ M or less.

The term "$k_{off}$" as used herein is intended to refer to the dissociation rate constant of a particular binding molecule-antigen interaction. The dissociation rate constant (koff+) can be measured using bio-layer interferometry, for example, using Octet™ system.

The term "epitope" as used herein is intended to refer to a portion (determinant) of an antigen that specifically binds to a binding molecule (for example, an antibody or a related molecule, such as a bispecific binding molecule). Epitope determinants usually consist of chemically active surface groupings of molecules such as amino acids or carbohydrates or sugar side chains and typically comprise specific three-dimensional structural characteristics, as well as specific charge characteristics. Epitopes can be either "linear" or "conformational". In a linear epitope, all of the points of interaction between a protein (e.g., an antigen) and an interacting molecule (such as an antibody) occur linearly along the primary amino acid sequence of the protein. In a conformational epitope, the points of interaction occur across amino acid residues on the protein that are separated from one another in the primary amino acid sequence. Once a desired epitope of an antigen is determined, it is possible to generate antibodies to that epitope using techniques well known in the art. In addition, generation and characterization of antibodies or other binding molecules may elucidate information about desirable epitopes. From this information, it is then possible to competitively screen antibodies for binding to the same or identical epitopes, e.g., by conducting competition studies to find binding molecules that compete with one another for binding to the antigen. As used herein, the term "epitope", inter alia, refers to a polypeptide fragment, having antigenic and/or immunogenic activity in animals, preferably in mammals such as mice and humans. The term "antigenic epitope" as used herein is a polypeptide fragment which can specifically bind to the antibody and can be detected by any technique well known from the prior art, for example, by a standard immunoassay. Antigen epitopes are not necessarily immunogenic; however, they can be immunogenic "Immunogenic epitope" as used herein is defined as a polypeptide fragment that evokes an antibody response in animals, as determined by any method known from the prior art. "Nonlinear epitope" or "conformational epitope" comprises nonadjacent polypeptides (or amino acids) within an antigen protein that binds to epitope-specific antibody.

One can determine whether an antibody or other binding molecule binds to the same epitope or cross-competes for binding with a PD-1 binding molecule of the present disclosure by using methods known in the art. In one embodiment, one allows a molecule of the disclosure to bind to PD-1 under saturating conditions and then measures the ability of the test antibody to bind to said target antigen. If the test antibody is able to bind to the target antigen at the same time as a reference binding molecule, then the test antibody binds to a different epitope than that of the reference binding molecule. However, if the test antibody is not able to bind to the target antigen at the same time, then the test antibody binds to the same epitope, an overlapping epitope, or an epitope that is in close proximity to the epitope bound to the binding molecule. This experiment can be performed using ELISA, RIA, BIACORE™, bio-layer interferometry or flow cytometry. To test whether a binding molecule of the disclosure cross-competes with another binding molecule, one may use the competition method described above in two directions, i.e. determining if the known binding molecule blocks the test binding molecule and vice versa. Such cross-competition experiments may be performed, e.g., using IBIS MX96 SPR or Octet™ system.

In one embodiment, a binding molecule of the disclosure is a monoclonal antibody. As used herein, the acronym "mAb" is intended to refer to a monoclonal antibody, i.e. an antibody synthesized and isolated by a separate clonal population of cells. A clonal population can be a clonal population of immortalized cells. In some embodiments, the immortalized cells in a clonal population are hybrid cells—hybridomas—typically produced by the fusion of individual B lymphocytes from immunized animals with individual cells from a lymphocytic tumour. Hybridomas are a type of constructed cells and do not exist in nature.

The class (isotype) and subclass of antibodies can be determined by any method known in the art. In general, the class and subclass of an antibody can be determined by antibodies specific to a certain class and subclass of antibodies. Such antibodies are commercially available. The class and subclass can be determined using ELISA, western blot analysis, and other methods. In another embodiment, the class and subclass can be determined by virtue of sequencing all or part of the heavy and/or light chain constant domains of antibodies, comparing amino acid sequences thereof with known amino acid sequences of various classes and subclasses of immunoglobulins, and determining the class and subclass of antibodies.

The terms "monoclonal antibody" or "monoclonal antibody composition" as used herein refer to a preparation of antibody molecules of a single molecular composition. A monoclonal antibody composition displays single binding specificity and affinity with respect to a particular antigen epitope.

The term "human antibody" as used herein is intended to include antibodies comprising variable regions in which both framework and CDRs are derived from human germ-line immunoglobulin sequences. Furthermore, if said antibody contains a constant region, the constant region is also derived from human germ-line immunoglobulin sequences.

The human antibodies of the disclosure may include amino acid residues not encoded by human germ-line immunoglobulin sequences (e.g., mutations introduced by random or site-specific in vitro mutagenesis, or an in vivo somatic mutation). However, the term "human antibody" as used herein is not intended to include antibodies in which CDR sequences derived from the germ-line of another mammalian species, such as a mouse, have been grafted onto human framework sequences.

The term "human monoclonal antibody" is intended to refer to antibodies displaying a single binding specificity which have variable regions in which both the framework and CDRs are derived from human germ-line immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and human light chain transgene fused to an immortalized cell.

The term "recombinant human antibody" as used herein includes all human antibodies that are prepared, expressed, engineered or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express a human antibody, e.g., from a transfectoma, (c) antibodies isolated from a recombinant, combinatorial human antibody library, and (d) antibodies prepared, expressed, engineered or isolated by any other means that involve splicing of human immunoglobulin gene sequences to other DNA sequences. Such recombinant human antibodies have variable regions in which framework regions and CDRs are derived from human germ-line immunoglobulin sequences. In certain embodiments, however, such recombinant human antibodies can be subjected to in vitro mutagenesis (or, when an animal transgenic for Ig sequences is used, somatic mutagenesis) and thus the amino acid sequences of the VH and VL regions of recombinant antibodies are sequences that, while derived from or related to human germ-line VH and VL sequences, may not naturally exist within the human antibody germ-line repertoire in vivo.

The phrases "an antibody recognizing an antigen" and "an antibody specific for an antigen" are used interchangeably herein with the term "an antibody which binds specifically to an antigen."

The term antibody "variant" as used herein is intended to refer to a molecule the amino acid sequence of which differs from a parental sequence by virtue of addition, deletion and/or, substitution of one or more amino acid residues in the sequence of a parental antibody. In a preferred embodiment, a variant antibody comprises at least one (for example, from one to about ten preferably 2, 3, 4, 5, 6, 7 or 8) amino acid addition, deletion and/or substitution in the CDRs of a parental antibody. This application defines identity or homology regarding the sequence of a variant antibody as the percentage of amino acid residues in a variant antibody sequence that are identical to residues in a parental antibody after aligning the sequences and, if needed, cutting in order to achieve a maximum percentage identical sequence. A variant antibody retains the ability to bind the same antigen or, preferably, epitope as that with which a parental antibody binds, or, preferably, exhibits at least one property or biological activity exceeding that of a parental antibody. For example, an antibody preferably has stronger affinity, longer half-life, lower IC50 or enhanced ability to inhibit antigen biological activity, as compared to a parental antibody. The variant antibody of particular interest herein is one which displays at least about 2-fold, preferably at least about 5-fold, 10-fold or 20-fold enhancement in biological activity as compared to a parental antibody.

The term "identity" or "homology" in the context of nucleic acid sequences is intended to refer to the residues in two sequences that are the same when aligned for maximum correspondence. Comparison of sequence identity may extend over a length of at least about nine nucleotides, commonly at least about 18 nucleotides, more commonly at least about 24 nucleotides, typically at least about 28 nucleotides, more typically at least about 32 nucleotides, and preferably at least about 36, 48 or more nucleotides. There are a number of various algorithms known in the art which can be used to measure nucleotide sequence identity. For example, polynucleotide sequences can be compared using FASTA, Gap or BESTFIT, which are programs in Wisconsin Package Version 10.0, Genetics Computer Group (GCG), Madison, Wis. FASTA, which includes, e.g., FASTA2 and FASTA3 programs, provides alignments and percent sequence identity of the regions of the best overlap between the query and search sequences (Pearson, Methods Enzymol. 183:63 98 (1990); Pearson, Methods Mol. Biol. 132: 185-219 (2000); Pearson, Methods Enzymol. 266: 227-258 (1996); Pearson, J. Mol. Biol. 276: 71-84 (1998)). Unless otherwise specified, default parameters for a particular program or algorithm are used. For instance, percent sequence identity between nucleic acid sequences can be determined using FASTA with default parameters (word size of 6 and NOPAM factor for the scoring matrix) or using Gap with default parameters as provided in GCG Version 6.1.

The term "homologous" with regard to a polypeptide sequence of an antibody should be construed as an antibody exhibiting at least 70%, preferably 80%, more preferably 90% and most preferably 95% sequence identity relative to a polypeptide sequence. The term in relation to a nucleic acid sequence should be construed as a sequence of nucleotides exhibiting at least 85%, preferably 90%, more preferably 95% and most preferably 97% sequence identity relative to a nucleic acid sequence.

As used herein, a "parental" antibody is an antibody encoded by an amino acid sequence, which is used for obtaining a variant.

The antibodies of the disclosure can be prepared by various design techniques, including using recombinant methods, including the shuffling of DNA obtained from various sources.

The term "humanized antibody" is intended to refer to antibodies in which CDR sequences derived from the germline of another mammalian species, such as a mouse, have been grafted onto human framework sequences. Additional framework region modifications may be made within such human framework sequences.

The term "chimeric antibody" is intended to refer to antibodies in which the variable region sequences are derived from one species and the constant region sequences are derived from another species, such as an antibody in which the variable region sequences are derived from a murine antibody and the constant region sequences are derived from a human antibody.

The term "specifically binds" as used herein is intended to refer to the situation in which one member of a specific binding pair does not significantly bind to molecules other than specific binding partner(s) thereof. The term is also applicable where e.g. an antigen-binding domain of an antibody of the disclosure is specific for a particular epitope that is carried by a number of antigens; in this case, the specific antibody comprising the antigen-binding domain will be able to specifically bind to various antigens carrying the epitope.

As used herein, an antibody that "specifically binds to human PD-1" is intended to refer to an antibody that binds to human PD-1 with KD of $1\times10^{-7}$ M or less, more preferably $5\times10^{-8}$ M or less, more preferably $1\times10^{-8}$ M or less, more preferably $5\times10^{-9}$ M or less.

The term "bispecific antibody" or "multispecific antibody" includes an antibody capable of selectively binding two or more epitopes. Bispecific antibodies, e.g., may comprise two different antigen-binding portions, wherein said antigen-binding portions specifically bind different epitopes either on different molecules (e.g., antigens), or on the same molecule (e.g., on the same antigen). If a bispecific antibody is able to selectively bind two different epitopes (a first epitope and second epitope), the affinity of the first antigen-binding portion for the first epitope will typically be at least one to two, or three, or four orders of magnitude lower than that of the first antigen-binding portion for the second epitope, and vice versa. Epitopes recognized by a bispecific antibody may be the same or different targets (e.g., on the same or a different protein). Bispecific antibodies can be prepared, for example, by combining heavy chains that recognize different epitopes on the same antigen. For example, nucleic acid sequences encoding variable heavy chain sequences that recognize different epitopes may be fused to nucleic acid sequences encoding various heavy chain constant regions, and such sequences may be expressed in a cell which expresses an immunoglobulin light chain. A typical bispecific antibody comprises two heavy chains, each comprising three heavy chain CDRs followed (from N-terminus to C-terminus) by a CH1 domain, hinge region, CH2 domain and CH3 domain, and immunoglobulin light chain which either does not have antigen-binding specificity but is able to combine with each of the heavy chains, or is able to combine with each of the heavy chains and bind one or more epitopes restricted by antigen-binding heavy chain regions, or is able to combine with each of the heavy chains and promotes binding of one or the both heavy chains to one or the both epitopes.

The phrases "biological property" or "bioactivity," "activity" or "biological activity," in reference to an antibody of the present disclosure, are used interchangeably herein and include, but are not limited to, epitope/antigen affinity and specificity, ability to neutralize or antagonize an activity of PD-1 in vivo or in vitro, IC50, the stability of an antibody and immunogenic properties of an antibody in vivo. Other identifiable biological properties of an antibody include, for example, cross-reactivity, (i.e., with non-human homologs of a target peptide, or with other proteins or tissues, generally), and an ability to preserve high levels of expression of protein in mammalian cells. Said properties or characteristics can be observed, measured or assessed using techniques recognized in the art, including, but not limited to, ELISA, competitive ELISA, antigen-antibody interactions by surface plasmon resonance using BIACORE or KINEXA, or bio-layer interferometry using ForteBio, in vitro or in vivo neutralization assays without limitation, receptor binding, production and/or secretion of a cytokine or growth factor, signal transduction and immunohistochemistry of tissue sections from various sources including human, primate, or any other source.

The term "inhibit" or "neutralize" as used herein with respect to the activity of an antibody of the disclosure is intended to refer to the ability to substantially antagonize, prohibit, prevent, restrain, slow, disrupt, eliminate, stop, reduce or reverse, e.g., progression or severity of that which is being inhibited including, but not limited to, a biological activity (e.g., the activity of PD-1) or property, disease or condition. The inhibition or neutralization of activity of PD-1 resulted from binding an antibody of the disclosure to PD-1 is preferably at least about 20%, 30%, 40%, 50%, 60%, 70%, 80%, 90%, 95% or higher.

PD-1 Binding Molecules

The present disclosure relates to a binding molecule that has the ability to bind to a human PD-1 receptor that contains an amino acid sequence that is at least 75% homologous to the sequence of SEQ ID NO:3, for example, at least 91%, 92%, 93% %, 94%, 95%, 96%, 97%, 98% or 99% identical to the sequence of SEQ ID NO:3.

In some embodiments, the heavy chain (HC) of an anti-PD1 antibody includes an amino acid sequence that is at least 60% identical to the sequence of SEQ ID NO:1, for example, at least 60%, 70% or 80% identical to the sequence of SEQ ID NO:1. In some embodiments, the heavy chain (HC) of the anti-PD1 antibody includes an amino acid that is at least 90% identical to the sequence of SEQ ID NO: 7, for example, at least 91%, 92%, 93%, 94%, 95%, 96%, 97%, 98%, or 99% identical to the sequence of SEQ ID NO: 7. In a particular embodiment, a LC comprises the amino acid sequence of SEQ ID NO: 5.

In some embodiments, the light chain of an anti-PD1 antibody comprises a light chain CDR1 (L-CDR1) amino acid sequence of SEQ ID NO:4, light chain CDR2 (L-CDR2) amino acid sequence of SEQ ID NO:5, light chain CDR3 (L-CDR3) amino acid sequence of SEQ ID NO:6, or any combination thereof. In some embodiments, the light chain of PD1 antibody comprises amino acid sequences L-CDR1, L-CDR2 and L-CDR3 shown in SEQ ID NOs: SEQ ID NO: 5 and SEQ ID NO: 6. In some embodiments, the light chain of an anti-PD1 antibody comprises a light chain variable domain (VL) that is at least 60% identical to the sequence of SEQ ID NO:8, for example, at least 60%, 70%, or 80% identical to the sequence SEQ ID NO:8. In some embodiments, the light chain of an anti-PD1 antibody comprises a light chain variable domain (VL) that is at least 90% identical to the sequence of SEQ ID NO:8, for example, at least 91%, 92%, 93%, 94%, 95%, 96%, 97%, 98% or 99% identical to the sequence of SEQ ID NO:8. In a particular embodiment, a VL domain comprises or consists of the amino acid sequence of SEQ ID NO:8.

In some embodiments, the light chain (LC) of an anti-PD1 antibody is at least 60% identical to the sequence of SEQ ID NO:10, for example, at least 60%, 70%, or 80% identical to the sequence of SEQ ID NO:10. In some embodiments, the light chain (LC) of a PD1 antibody is at least 90% identical to the sequence of SEQ ID NO:10, for example, at least 91%, 92%, 93%, 94%, 95%, 96% 97%, 98%, or 99% identical to the sequence of SEQ ID NO: 10. In a particular embodiment, a VL domain comprises or consists of the amino acid sequence of SEQ ID NO:10.

The class of a binding molecule obtained using techniques described herein may be switched with another class or subclass. In one aspect of the disclosure, a nucleic acid molecule encoding a VL or VH is isolated using methods well-known in the art such that it does not include nucleic acid sequences encoding a CL or CH. The nucleic acid molecules encoding VL or VH were operatively linked to a nucleic acid sequence encoding a CL or CH, respectively, from a different class of immunoglobulin molecule. This may be achieved using a vector or nucleic acid molecule that comprises a CL or CH chain, as described above. For example, a binding molecule that was originally IgM may be class-switched to IgG. Further, class-switching may be used to convert one IgG subclass to another, e.g., from IgG1 to IgG2. An exemplary method for producing a binding molecule of the disclosure with a desired isotype comprises the steps of isolating a nucleic acid molecule encoding the heavy chain of a binding molecule and a nucleic acid molecule encoding the light chain of a binding molecule, obtaining the variable domain of the heavy chain, ligating the variable domain of the heavy chain with the constant domain of a heavy chain of the desired isotype, expressing the light chain and the ligated heavy chain in a cell, and obtaining the binding molecule with the desired isotype.

A binding molecule of the disclosure can be an IgG, IgM, IgE, IgA, or IgD molecule, but is typically of the IgG isotype, e.g., IgG1, IgG2a or b, IgG3, or IgG4 of the IgG subclass. In one embodiment, a binding molecule is an IgG1 antibody of the IgG subclass.

In one embodiment, a binding molecule may comprise at least one mutation in the Fc region. A number of various Fc mutations are known, where these mutations provide altered effector function. For example, in many cases it will be desirable to reduce or eliminate the effector function, e.g., where ligand-receptor interaction is undesired or in the case of antibody-drug conjugates. Amino acid Fc region positions, which can be advantageously mutated to reduce the effector function, include one or more of positions 228, 233, 234 and 235, wherein amino acid positions are numbered according to the Kabat numbering scheme. In some embodiments, the binding molecule comprises an Fc region of at least one mutation that reduces ADCC and/or CDC, compared with the same binding molecule without mutations.

In some embodiments, a binding molecule of the disclosure may be part of a larger immunoadhesion molecule formed by covalent or noncovalent association of an antibody or antibody portion with one or more other proteins or peptides. Examples of such immunoadhesion molecules include use of a streptavidin core region to make a tetrameric scFv molecule (Kipriyanov et al., Human Antibodies and Hybridomas 6:93-101 (1995)) and use of a cysteine residue, a marker peptide and a C-terminal polyhistidine tag to make bivalent and biotinylated scFv molecules (Kipriyanov et al., Mol. Immunol. 31:1047-1058 (1994)). Other examples include where one or more CDRs from an antibody are incorporated into a molecule either covalently or noncovalently to produce an immunoadhesin that specifically binds to the antigen of interest. In such embodiments, CDRs may be incorporated as part of a larger polypeptide chain, may be covalently linked to another polypeptide chain, or may be incorporated noncovalently.

In a further embodiment, a fusion antibody or immunoadhesin may be produced which comprises all or a portion of a binding molecule of the disclosure linked to another polypeptide. In some embodiments, only the variable regions of a binding molecule are linked to a polypeptide. In some embodiments, the VH domain of a binding molecule is linked to a first polypeptide, while the VL domain of a binding molecule is linked to a second polypeptide that associates with the first polypeptide in a manner in which the VH and VL domains can interact with one another to form an antigen-binding site. In another preferred embodiment, the VH domain is separated from the VL domain by a linker such that the VH and VL domains can interact with one another (e.g., single chain antibodies). The VH-linker-VL antibody is then linked to the polypeptide of interest. Furthermore, fusion antibodies can be created in which two (or more) single chain antibodies are linked to one another. This is useful if one wants to engineer a bivalent or polyvalent antibody on a single polypeptide chain, or if one wants to engineer multispecific antibodies.

To engineer a single chain antibody (scFv), VH- and VL-encoding DNA fragments are operatively linked to another fragment encoding a flexible linker, e.g., encoding an amino acid sequence (Gly4-Ser)3 such that the VH and VL sequences can be expressed as a contiguous single chain protein with the VL and VH domains joined by a flexible linker. See, e.g., Bird et al., Science 242:423 426 (1988); Huston et al., Proc. Natl. Acad. Sci. USA 85:5879 5883 (1988); and McCafferty et al., Nature 348:552 554 (1990). The single chain antibody may be monovalent, if only a single VH and VL domain are used, bivalent, if two VH and VL domains are used, or polyvalent, if more than two VH and VL domains are used.

A binding molecule of the disclosure can be derivatized or linked to another molecule (e.g., another peptide or protein). In general, binding molecules (e.g., antibodies or antigen-binding portions thereof) are derivatized such that the PD-1 binding is not affected adversely by derivatization or labeling. Thus, the binding molecules of the disclosure can include both intact and modified forms of binding molecules described herein. For example, a binding molecule of the disclosure can be functionally linked (by virtue of chemical coupling, genetic fusion, noncovalent association or otherwise) to one or more molecular entities, such as another antibody, a detection agent, a pharmaceutical agent, and/or a protein or peptide that can mediate association of the binding molecule with another molecule (such as a streptavidin core region or polyhistidine tag).

One type of a derivatized binding molecule is produced by crosslinking two or more antibodies (of the same type or of different types, e.g., to engineer bispecific antibodies). Suitable crosslinkers include those that are heterobifunctional, having two different reactive groups separated by a suitable spacer (e.g., m-maleimidobenzoyl-N-hydroxysuccinimide ester) or homobifunctional (e.g., disuccinimidyl suberate).

A binding molecule of the disclosure may also be derivatized with a chemical group such as polyethylene glycol (PEG), a methyl or ethyl group, or a carbohydrate group. These groups may be useful to improve the biological characteristics of a binding molecule, e.g., to increase serum half-life.

A binding molecule of the disclosure can also be labeled. As used herein, the terms "label" or "labeled" refer to incorporation of another molecule in a binding molecule. In one embodiment, a label is a detectable marker, e.g., incorporation of a radioactive amino acid or attachment of biotinyl fragments to a polypeptide, and such fragments can be detected by labeled avidin (e.g., streptavidin comprising a fluorescent marker or enzymatic activity that can be detected by optical or colorimetric techniques). In a further embodiment, a label or marker can be therapeutic, e.g., a drug conjugate or toxin. Various methods of labeling polypeptides and glycoproteins are known in the art and may be used. Examples of labels for polypeptides include, inter alia, the following: radioisotopes or radionuclides (e.g., 3H, 14C, 15N, 35S, 90Y, 99Tc, 111In, 125I, 131I), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

In certain embodiments, the binding molecules of the disclosure may be present in a neutral form (including zwitterionic forms) or as a positively or negatively charged species. In some embodiments, the antibodies may be complexed with a counterion to form a pharmaceutically acceptable salt.

The term "pharmaceutically acceptable salt" is intended to refer to a complex comprising one or more binding molecules and one or more counterions, where the counterions are derived from pharmaceutically acceptable inorganic and organic acids and bases.

Pharmaceutically acceptable inorganic bases include metallic ions including, inter alia, suitable alkali metal salts, alkaline earth metal salts and other physiological ions of acceptable metals. Salts derived from inorganic bases include aluminum, ammonium, calcium, cobalt, nickel, molybdenum, vanadium, manganese, chromium, selenium, tin, copper, ferric, lithium, magnesium, manganic or manganous, potassium, rubidium, sodium, and zinc salts, and in their typical valences.

Pharmaceutically acceptable acid addition salts of the binding molecules of the disclosure can be prepared from the following acids, including, inter alia, formic, acetic, acetamidobenzoic, adipic, ascorbic, boric, propionic, benzoic, camphoric, carbonic, cyclamic, dehydrocholic, malonic, edetic (ethylenediaminetetraacetic), ethylsulfuric, fendizoic, metaphosphoric, succinic, glycolic, gluconic, lactic, malic, tartaric, tannic, citric, nitric, glucuronic, maleic, folic, fumaric, pyruvic, aspartic, glutamic, hydrochloric, hydrobromic, hydroiodic, lysine, isocitric, trifluoroacetic, pamoic, anthranilic, mesylic, orotic, oxalic, oxalacetic, oleic, stearic, salicylic, aminosalicylic, silicate, p-hydroxybenzoic, nicotinic, phenylacetic, mandelic, embonic, sulfonic, methanesulfonic, phosphoric, phosphonic, ethanesulfonic, ethanedisulfonic, ammonium, benzenesulfonic, pantothenic, naphthalenesulfonic, toluenesulfonic, 2-hydroxyethanesulfonic, sulfanilic, sulfuric, nitric, nitrous, sulfuric acid monomethyl ester, cyclohexylaminosulfonic, β-hydroxybutyric, glycine, glycylglycine, cacodylate, diaminohexanoic, camphorsulfonic, thiocyanic, oxoglutaric, pyridoxal 5-phosphate, chlorophenoxyacetic, undecanoic, N-acetyl-L-aspartic, galactaric and galacturonic acids.

Pharmaceutically acceptable organic bases include trimethylamine, diethylamine, N,N'-dibenzylethylenediamine, chloroprocaine, choline, dibenzylamine, diethanolamine, ethylenediamine, meglumine (N-methylglucamine), procaine, cyclic amines, quaternary ammonium cations, arginine, betaine, caffeine, clemizole, 2-ethylaminoethanol, 2-diethylaminoethanol, 2-dimethylaminoethanol, ethanediamine, butylamine, ethanolamine, ethylenediamine, N-ethylmorpholine, N-ethylpiperidine, ethylglucamine, glucamine, glucosamine, histidine, hydrabamine, imidazole, isopropylamine, methylglucamine, morpholine, piperazine, pyridine, pyridoxine, neodymium, piperidine, polyamine resins, procaine, purines, theobromine, triethylamine, tripropylamine, triethanolamine, tromethamine, methylamine, taurine, cholate, 6-amino-2-methyl-2-heptanol, 2-amino-2-methyl-1,3-propanediol, 2-amino-2-methyl-1-propanol, aliphatic mono- and dicarboxylic acids, phenyl-substituted alkanoic acids, hydroxy alkanoic acids, aromatic acids, aliphatic and aromatic sulfonic acids, strontium, tricine, hydrazine, phenylcyclohexylamine, 2-(N-morpholino)ethanesulfonic acid, bis(2-hydroxyethyl)amino-tris(hydroxymethyl)methane, N-(2-acetamido)-2-aminoethanesulfonic acid, 1,4-piperazinediethanesulfonic acid, 3-morpholino-2-hydroxypropanesulfonic acid, 1,3-bis[tris(hydroxymethyl)methylamino]propane, 4-morpholinepropanesulfonic acid, 4-(2-hydroxyethyl)piperazine-1-ethanesulfonic acid, 2-[(2-hydroxy-1,1-bis(hydroxymethyl)ethyl)amino] ethanesulfonic acid, N,N-bis(2-hydroxyethyl)-2-aminoethanesulfonic acid, 4-(N-morpholino)butanesulfonic acid, 3-(N,N-bis[2-hydroxyethyl]amino)-2-hydroxy propanesulfonic acid, 2-hydroxy-3-[tris (hydroxymethyl)methylamino]-1-propanesulfonic acid, 4-(2-hydroxyethyl)piperazine-1-(2-hydroxypropane sulfonic acid), piperazine-1,4-bis(2-hydroxypropanesulfonic acid) dihydrate, 4-(2-hydroxyethyl)-1-piperazinepropanesulfonic acid, N,N-bis(2-hydroxyethyl) glycine, N-(2-hydroxyethyppiperazine-N'-(4-butanesulfonic acid), N-[tris(hydroxymethyl)methyl]-3-aminopropanesulfonic acid, N-tris(hydroxymethyl)methyl-4-aminobutanesulfonic acid, N-(1,1-dimethyl-2-hydroxyethyl)-3-amino-2-hydroxy propanesulfonic acid, 2-(cyclohexylamino) ethanesulfonic acid, 3-(cyclohexylamino)-2-hydroxy-1-propanesulfonic acid, 3-(cyclohexylamino)-1-propanesulfonic acid, N-(2-acetamido)iminodiacetic acid, 4-(cyclohexylamino)-1-butanesulfonic acid, N-[tris(hydroxymethyl)methyl] glycine, 2-amino-2-(hydroxymethyl)-1,3-propanediol, and trometamol.

Nucleic Acid Molecules and Vectors

The present disclosure also relates to nucleic acid molecules, and sequences encoding the binding molecules of the disclosure described herein. In some embodiments, various nucleic acid molecules encode the first domain and second domain of the amino acid sequence of a binding molecule. In some embodiments, wherein a first domain and/or second domain comprises a heavy chain and light chain, various nucleic acids encode a heavy chain and light chain amino acid sequences. In other embodiments, the same nucleic acid molecule encodes a heavy chain and light chain amino acid sequences. In certain embodiments, a nucleic acid molecule can encode any combination of amino acid sequences (e.g., heavy and light chain sequences) of first and second domains. In a particular embodiment, a nucleic acid molecule can encode the amino acid sequence of a first binding domain and the light chain amino acid sequence of a second binding domain, optionally including any sequence of a peptide linker connecting them.

A reference to a nucleotide sequence encompasses the complement thereof unless otherwise specified. Thus, a reference to a nucleic acid having a particular sequence should be understood as one which encompasses the complementary strand thereof with the complementary sequence thereof. The term "polynucleotide" as used herein means a polymeric form of either nucleotides that are at least 10 bases in length, or ribonucleotides, or deoxyribonucleotides or a modified form of either type of nucleotide. The term includes single and double stranded forms.

The present disclosure also relates to nucleotide sequences that are at least 70%, 75%, 80%, 85%, 90%, 95%, 97%, 98%, or 99% identical to one or more of said nucleotide sequences or a nucleotide sequence encoding an amino acid sequence selected from a group consisting of SEQ ID NO: 1-10. In certain embodiments, nucleotide sequences are at least 90%, 91%, 92%, 93%, 94%, 95%, 96%, 97%, 98% or 99% identical to a nucleotide sequence encoding an amino acid sequence selected from a group consisting of SEQ ID NO: 4-9. The term "percent sequence identity" in the context of nucleic acid sequences is intended to refer to the residues in the two sequences which are the same when aligned for maximum correspondence. Comparison of sequence identity may extend over a length of at least about nine nucleotides, commonly at least about 18 nucleotides, more commonly at least about 24 nucleotides, typically at least about 28 nucleotides, more typically at least about 32 nucleotides, and preferably at least about 36, 48 or more nucleotides. There are a number of various algorithms known in the art which can be used to measure nucleotide sequence identity. For example, polynucleotide sequences can be compared using FASTA, Gap or BESTFIT, which are programs in Wisconsin Package Version 10.0, Genetics Computer Group (GCG), Madison, Wis. FASTA, which includes, e.g., FASTA2 and FASTA3 programs, provides alignments and percent sequence identity of the regions of the best overlap between the query and search sequences (Pearson, Methods Enzymol. 183:63 98 (1990); Pearson, Methods Mol. Biol. 132: 185-219 (2000); Pearson, Methods Enzymol. 266: 227-258 (1996); Pearson, J. Mol. Biol. 276: 71-84 (1998); incorporated herein by reference). Unless otherwise specified, default parameters for a particular program or algorithm are used. For example, percent sequence identity between nucleic acid sequences can be determined using FASTA with default parameters (word size of 6 and NOPAM factor for the scoring matrix) or using Gap with default parameters as provided in GCG Version 6.1, herein incorporated by reference.

In one aspect, the present disclosure relates to a nucleic acid molecule comprising a nucleotide sequence encoding an amino acid sequence selected from SEQ ID NO: 1-10. A nucleic acid molecule can also comprise any combination of said nucleotide sequences. In one embodiment, a nucleic acid molecule comprises a nucleotide sequence encoding SEQ ID NO: 4. In a further embodiment, a nucleic acid molecule comprises a nucleotide sequence encoding SEQ ID NO: 4 and 6. In a further embodiment, a nucleic acid molecule comprises a nucleotide sequence encoding SEQ ID NO: 4, 6 and 16. In a further embodiment, a nucleic acid molecule comprises a nucleotide sequence encoding SEQ ID NO: 7. In a further embodiment, a nucleic acid molecule comprises a nucleotide sequence encoding SEQ ID NO: 5.

In any of the above embodiments, nucleic acid molecules can be isolated.

In another aspect, the present disclosure relates to a vector suitable for the expression of any of nucleotide sequences described herein. The term "vector" as used herein means a nucleic acid molecule capable of transporting another nucleic acid to which it has been linked. In some embodiments, a vector is a plasmid, i.e., a circular double stranded piece of DNA into which additional DNA segments may be ligated. In some embodiments, a vector is a viral vector, wherein additional DNA segments may be ligated into the viral genome. In some embodiments, vectors are capable of autonomous replication in a host cell into which they are introduced (e.g., bacterial vectors having a bacterial origin site of replication and episomal mammalian vectors). In further embodiments, vectors (e.g., non-episomal mammalian vectors) can be integrated into the genome of a host cell upon introduction into a host cell, and thereby are replicated along with the host gene. Moreover, certain vectors are capable of directing the expression of genes to which they are operatively linked. Such vectors are referred to herein as "recombinant expression vectors" (or simply, "expression vectors").

The present disclosure relates to vectors comprising nucleic acid molecules that encode any of the amino acid sequences of binding molecules or portions thereof (e.g., heavy and/or light chain sequences of the first and/or second binding domains) as described herein. The disclosure further provides vectors comprising nucleic acid molecules encoding fusion proteins, modified antibodies, antibody fragments, and probes thereof.

A nucleic acid molecule of the disclosure can be isolated from any source that produces binding molecule or a portion thereof. In certain embodiments, a nucleic acid molecule of the disclosure can be synthesized, rather than isolated.

In some embodiments, a nucleic acid molecule of the disclosure can comprise a nucleotide sequence encoding a VH domain from the first or second domain of a binding molecule of the disclosure, joined in-frame to a nucleotide sequence encoding a heavy chain constant domain from any source. Similarly, a nucleic acid molecule of the disclosure can comprise a nucleotide sequence encoding a VL domain from the first or second region of a binding molecule of the disclosure, joined in-frame to a nucleotide sequence encoding a light chain constant domain from any source.

In a further aspect of the disclosure, nucleic acid molecules encoding the variable domain of heavy (VH) and/or light (VL) chains of a first or second binding domain may be "converted" throughout the length of antibody genes. In one embodiment, nucleic acid molecules encoding VH or VL domains are converted to antibody genes along the entire the length by virtue of insertion into an expression vector already encoding heavy chain constant (CH) or light chain constant (CL) domains, respectively, such that the VH segment is operatively linked to the CH segment(s) within the vector, and/or the VL segment is operatively linked to the CL segment within the vector. In another embodiment, nucleic acid molecules encoding the VH and/or VL domains are converted into antibody genes throughout the length by virtue of linking, e.g., ligating, a nucleic acid molecule encoding VH and/or VL domains to a nucleic acid molecule encoding CH and/or CL domains using standard molecular biological techniques. Nucleic acid molecules encoding heavy and/or light chains throughout the length may then be expressed from a cell into which they have been introduced.

Nucleic acid molecules may be used to express large quantities of recombinant binding molecules. Nucleic acid molecules may also be used to produce human antibodies, humanized antibodies, chimeric antibodies, bispecific antibodies, single chain antibodies, immunoadhesins, diabodies, mutated antibodies and antibody derivatives, as described herein.

In another embodiment, a nucleic acid molecule of the disclosure is used as a probe or PCR primer for a specific antibody sequence. For example, a nucleic acid can be used as a probe in diagnostic techniques or as a PCR primer to amplify regions of DNA that could be used, e.g., to isolate additional nucleic acid molecules encoding binding molecule regions (e.g., variable domains). In some embodiments, nucleic acid molecules are oligonucleotides. In some embodiments, oligonucleotides are from highly variable domains of a binding molecule. In some embodiments, oligonucleotides encode all or a part of one or more of the CDRs of a binding molecule of the disclosure as described herein.

In another embodiment, nucleic acid molecules and vectors may be used to make mutated binding molecules. Antibodies may be mutated in the variable domains of the heavy and/or light chains of a first and/or second binding domain, e.g., to alter a binding property of a binding molecule. For example, a mutation may be made in one or more of CDRs to increase or decrease the KD of a binding molecule, to increase or decrease koff, or to alter the binding specificity of an antibody with respect to PD-1. In another embodiment, one or more mutations are made at an amino acid residue that is known to be changed compared to the germ-line in an antibody corresponding to the first or second binding domain of a binding molecule of the disclosure. Such mutations may be made in the CDR or framework region of a variable domain, or in a constant domain. In a preferred embodiment, mutations are made in a variable domain. In another embodiment, one or more mutations are made at an amino acid residue that is known to be changed compared to the germ-line in the CDR or framework region of a variable domain of a binding molecule of the disclosure.

In another embodiment, a framework region(s) is mutated so that the resulting framework region(s) has the amino acid sequence of the corresponding germ-line gene. Such mutations may be made in a framework region or constant domain to increase the half-life of a binding molecule. See, e.g., WO 00/09560. A mutation in a framework region or constant domain can also be made to alter the immunogenicity of a binding molecule and/or to provide a site for covalent or non-covalent binding to another molecule. According to the disclosure, a binding molecule may have mutations in any one or more of the CDRs or framework regions of a variable domain or in a constant domain.

In some embodiments, the binding molecules of the disclosure are expressed by inserting a DNA partially or fully encoding the sequence of a first or second binding domain (e.g., light and heavy chain sequences where a binding domain comprises light and heavy chain sequences), obtained as described above, in expression vectors such that the genes are operatively linked to necessary expression control sequences, such as transcriptional and translational control sequences. Expression vectors include plasmids, retroviruses, adenoviruses, adeno-associated viruses (AAV), plant viruses, such as cauliflower mosaic virus, tobacco mosaic virus, cosmids, YACs, EBV derived episomes, and the like. DNA molecules may be ligated into a vector such that transcriptional and translational control sequences within the vector serve their intended function of regulating the transcription and translation of the DNA. An expression vector and expression control sequences may be chosen to be compatible with the expression host cell used. DNA molecules partially or fully encoding the sequences of first and second binding domains (for example, heavy and light chain sequences where a binding domain comprises a heavy and light chain sequence) can be introduced into individual vectors. In one embodiment, any combination of said DNA molecules is introduced into the same expression vector. DNA molecules can be introduced into an expression vector by standard methods (e.g., ligation of complementary restriction sites on an antibody gene fragment and vector, or blunt end ligation if no restriction sites are present).

A suitable vector is one that encodes functionally complete human CH or CL immunoglobulin sequences, with appropriate restriction site engineering so that any VH or VL sequence can easily be inserted and expressed, as described above. HC- and LC-encoding genes in such vectors may contain intron sequences that results in enhanced overall antibody protein yields by stabilizing the corresponding mRNA. The intron sequences are flanked by splice donor and splice acceptor sites, which determine where RNA splicing will occur. Location of intron sequences can be either in variable or constant regions of antibody chains, or in both variable and constant regions when multiple introns are used. Polyadenylation and transcription termination may occur at a native chromosomal site downstream of coding regions. A recombinant expression vector can also encode a signal peptide that facilitates secretion of an antibody chain from a host cell. An antibody chain gene may be cloned into a vector such that the signal peptide is linked in-frame to the amino terminus of an immunoglobulin chain. The signal peptide can be an immunoglobulin signal peptide or a heterologous signal peptide (i.e., a signal peptide from a non-immunoglobulin protein).

In addition to antibody chain genes, the recombinant vector expression of the disclosure can carry regulatory sequences that control the expression of antibody chain genes in a host cell. It will be understood by those skilled in the art that the design of an expression vector, including the selection of regulatory sequences, may depend on such factors as the choice of a host cell to be transformed, the level of expression of a desired protein, and so forth. Preferred control sequences for an expression host cell in mammals include viral elements that ensure high levels of protein expression in mammalian cells, such as promoters and/or enhancers derived from a retroviral LTR, cytomegalovirus (CMV) (such as a CMV promoter/enhancer), simian virus 40 (SV40) (such as a SV40 promoter/enhancer), adenovirus, (e.g., the adenovirus major late promoter (AdMLP)), polyomavirus and strong mammalian promoters such as native immunoglobulin and actin promoters. For further description of viral control elements and sequences thereof, see, e.g., U.S. Pat. Nos. 5,168,062, 4,510,245 and 4,968,615. Methods for expressing binding molecules, such as antibodies in plants, including a description of promoters and vectors, as well as transformation of plants is known in the art. See, e.g., U.S. Pat. No. 6,517,529. Methods for expressing polypeptides in bacterial cells or fungal cells, e.g., yeast cells, are also well known in the art.

In addition to antibody chain genes and regulatory sequences, the recombinant expression vectors of the disclosure may carry additional sequences, such as sequences that regulate replication of a vector in host cells (e.g., origins of replication) and selectable marker genes. The selectable marker gene facilitates the selection of host cells into which a vector has been introduced (see e.g., U.S. Pat. Nos. 4,399,216, 4,634,665 and 5,179,017). For example, typically the selectable marker gene confers resistance to medicinal agents, such as G418, hygromycin or methotrexate, to a host cell into which a vector has been introduced. For example, selectable marker genes include a dihydrofolate reductase (DHFR) gene (for use in dhfr-host cells during methotrexate selection/amplification), a neo gene (for G418 selection), and a glutamate synthetase gene.

The term "expression control sequence" as used herein is intended to refer to polynucleotide sequences that are necessary to affect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include the promoter of a ribosomal binding site, and transcription termination sequences; in eukaryotes, typically, such control sequences include promoters and transcription termination sequences. The term "control sequences" is intended to include at least all components, the presence of which is essential for expression and processing, and can also include additional components, the presence of which is advantageous, for example, leader sequences and fusion partner sequences.

Host Cells and a Method for Producing a Binding Molecule

A further aspect of the disclosure relates to methods for producing binding molecules of the disclosure. One embodiment of the disclosure relates to a method for producing binding molecules as defined herein, comprising introducing a recombinant host cell capable of expressing a binding molecule, cultivating said host cells under conditions suitable for expression of the binding molecule, and isolating the obtained binding molecule. Binding molecules produced by such expression in such recombinant host cells are referred to herein as "recombinant binding molecules." Where the binding molecules are antibodies, they are called "recombinant antibodies". The disclosure also relates to the progeny of cells from such host cells and binding molecules obtained analogously.

The term "recombinant host cell" (or simply "host cell") as used herein is intended to refer to a cell into which a recombinant expression vector has been introduced. The present disclosure relates to host cells, which may include, for example, a vector according to the disclosure described above. The present disclosure also relates to host cells that comprise, for example, a nucleotide sequence encoding a heavy chain or antigen-binding portions thereof, a light chain-encoding nucleotide sequence or antigen-binding portions thereof, or both, of the first binding domain and/or second binding domain of a binding molecule of the disclosure. It should be understood that "recombinant host cell" and "host cell" are intended to refer not only to a particular subject cell but to the progeny of such a cell as well. Since modifications may occur in succeeding generations due to either mutation or environmental influences, such progeny may not, in fact, be identical to a parental cell, however, such cells are still included within the scope of the term "host cell" as used herein.

Nucleic acid molecules encoding the binding molecules of the disclosure and vectors comprising these nucleic acid molecules can be used for transfection of a suitable mammalian, plant, bacterial or yeast host cell. Transformation can be by any known technique for introducing polynucleotides into a host-cell. Methods for introduction of heterologous polynucleotides into mammalian cells are well known in the art and include dextran—mediated transfection, calcium phosphate precipitation, polybrene—mediated transfection, protoplast fusion, encapsulation of the polynucleotide(s) in liposomes, and direct microinjection of DNA into nuclei. In addition, nucleic acid molecules may be introduced into mammalian cells by viral vectors. Methods for transforming cells are well known in the art. See, e.g., U.S. Pat. Nos. 4,399,216, 4,912,040, 4,740,461 and 4,959,455. Methods for transforming plant cells are well known in the art, including, e.g., *Agrobacterium*-mediated transformation, biolistic transformation, direct injection, electroporation and viral transformation. Methods of transforming bacterial and yeast cells are also well known in the art.

Mammalian cell lines available as hosts for expression are well known in the art and include a plurality of immortalized cell lines available from the American Type Culture Collection (ATCC). These include, inter alia, Chinese hamster ovary (CHO) cells, NSO cells, SP2 cells, HEK-293T cells, FreeStyle 293 cells (Invitrogen), NIH-3T3 cells, HeLa cells, baby hamster kidney (BHK) cells, African green monkey kidney cells (COS), human hepatocellular carcinoma cells (e.g., Hep G2), A549 cells, and a number of other cell lines. Cell lines of particular preference are selected through determining which cell lines have high expression levels. Other cell lines that may be used are insect cell lines, such as Sf9 or Sf21 cells. When recombinant expression vectors encoding binding molecules are introduced into mammalian host cells, the binding molecules are produced by culturing the host cells for a period of time sufficient to allow for expression of binding molecules in host cells or, more preferably, secretion of a binding molecule into the culture medium in which the host cells are grown. Binding molecules can be reconstituted from the culture medium using standard protein purification techniques. Plant host cells include, e.g., *Nicotiana, Arabidopsis*, duckweed, corn, wheat, potato, etc. Bacterial host cells include *E. coil* and *Streptomyces* species. Yeast host cells include *Schizosaccharomyces pombe, Saccharomyces cerevisiae* and *Pichia pastoris*.

Furthermore, expression of the binding molecules of the disclosure from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, 0 323 997 and 0 338 841.

It is likely that binding molecules expressed by different cell lines or in transgenic animals will have a different glycosylation profile as compared to each other. However, all binding molecules encoded by the nucleic acid molecules described herein, or comprising the amino acid sequences provided herein are part of the present disclosure, regardless of the glycosylation of the binding molecules, and, in general, regardless of the presence or absence of post-translational modifications.

The binding molecules can be produced using a plurality of methods. For example, PD1-binding domains can be prepared separately (e.g., using chemical protein synthesis, recombinant expression techniques, hybridoma technology, etc.) and then chemically attached to each other, directly or via a linker. Means for chemical conjugation of molecules (e.g., antibodies or antigen-binding portions thereof) are well known in the art. Polypeptides typically contain a variety of functional groups, such as carboxylic acid (COOH) or free amine (—NH2) groups, which are capable of reacting with a suitable functional group of a corresponding polypeptide or linker. An antibody can also be derivatized to expose or attach additional reactive functional groups and may include attachment of any of a number of linker molecules such as those available from Pierce Chemical Company, Rockford, Ill. The linkers used in the binding molecules of the disclosure can be any of suitable linkers known in the art.

In some embodiments, the binding of domains to PD1 is produced by the expression of recombinant antibodies or antigen-binding portions thereof in host cells. Sequences encoding any combination of binding domains may be linked (directly or through a linker). The obtained nucleic acid molecules encoding the domains which bind to PD-1 are inserted into expression vectors and introduced into host cells. The obtained binding molecules then are expressed, isolated and purified from the expression system.

In some embodiments, binding domains of a binding molecule may be coupled together by an innovative linker molecule intended for protection against the proteolytic degradation of a binding molecule. Such a linker is typically devoid of a proteolytic cleavage site.

As used herein, the expressions "cell," "host cell," "cell line," and "cell culture," "cell line as a producer" are used interchangeably and include an individual cell or cell culture that is a recipient of any isolated polynucleotide of the disclosure or any recombinant vector (any recombinant vectors) that comprise a sequence encoding an HCVR, LCVR or monoclonal antibody of the disclosure. Host cells include the progeny of a single host cell, and the progeny may not necessarily be completely identical (in morphology or in total DNA complement) to the original parental cell due to natural, accidental, or deliberate mutation and/or alterations. A host cell includes cells transformed, transduced or infected with a recombinant vector, or a monoclonal antibody that expresses a polynucleotide of the disclosure or a light or heavy chain thereof. A host cell which comprises a recombinant vector of the disclosure (either stably incorporated into host chromosomes or not) may also be referred to as a "recombinant host cell". Preferred host cells for use in the disclosure are CHO cells (e.g., ATCC CRL-9096), NSO cells, SP2/0 cells, COS cells (ATCC, e.g., CRL-1650, CRL-1651), and HeLa (ATCC CCL-2). Additional host cells for use in the disclosure include plant cells, yeast cells, other mammalian cells and prokaryotic cells.

Pharmaceutical Composition

The term "pharmaceutical composition" is intended to refer to a formulation and/or composition containing a therapeutically effective amount of an antibody of the disclosure plus excipients (diluents, vehicles, solvents and other excipients).

The term "excipient" is used herein to describe any ingredient other than the compound(s) of the disclosure. The choice of an excipient depends largely on factors such as the particular technique of administration, the effect of an excipient on solubility and stability, and the nature of a dosage form. As used herein, "pharmaceutically acceptable excipient" includes any and all solvents, dispersion media, coatings, antibacterial and antifungal agents, isotonic and absorption delaying agents and similar physiologically compatible substances. Examples of said pharmaceutically acceptable excipients are water, physiologic saline, phosphate buffer, dextrose, glycerol, ethanol, etc., and combinations thereof. It is often preferable to add to the composition isotonic agents, e.g., sugars, polyalcohols, such as mannitol or sorbitol, or sodium chloride. The further examples of pharmaceutically acceptable excipients are wetting agents or a small amount of auxiliary substances, such as moisturizers and emulsifiers, preservatives or buffers that will increase the storage duration and efficiency of an antibody.

An antibody of the disclosure can be incorporated into a pharmaceutical composition suitable for administration to a patient (see Example 17). The antibodies of the disclosure may be administered alone or in combination with a pharmaceutically acceptable carrier, diluent, and/or excipient, in single or multiple doses. Pharmaceutical compositions for administration are designed to be appropriate for the selected mode of administration, and pharmaceutically acceptable diluents, carriers, and/or excipients, such as dispersing agents, buffers, surfactants, preservatives, solubilizing agents, isotonicity agents, stabilizing agents and the like be used as appropriate (see Example 17). Said compositions are designed in accordance with conventional techniques as in e.g., Remington, The Science and Practice of Pharmacy, 19th Edition, Gennaro, Ed., Mack Publishing Co., Easton, Pa. 1995, which provides various techniques for obtaining the compositions as are generally known to a skilled person.

A composition comprising an anti-PD-1 monoclonal antibody of the disclosure may be administered to a patient exhibiting the risk of adverse development or pathologies as described herein using standard administration techniques, including peroral, intravenous, intraperitoneal, subcutaneous, pulmonary, transdermal, intramuscular, intranasal, buccal, sublingual, or suppository administration.

A pharmaceutical composition of the disclosure preferably comprises or is a "therapeutically effective amount" of an antibody of the disclosure. The term "therapeutically effective amount" is intended to refer to an amount that is effective, at dosages and for periods of time necessary, to achieve the desired therapeutic result. A therapeutically effective amount of an antibody may vary according to factors such as disease state, age, sex and weight of a subject, and the ability of an antibody or part thereof to elicit a desired response in a subject.

A therapeutically effective amount is also one in which any toxic or detrimental effects of the antibody are outweighed by the therapeutically beneficial effects. "Prophylactically effective amount" is intended to refer to the amount that is effective, at dosages and for periods of time necessary to achieve the desired prophylactic result. Since a prophylactic dose is prescribed for individuals before or at an early stage of disease, typically a prophylactically effective amount may be less than a therapeutically effective amount.

A therapeutically effective or prophylactically effective amount is at least a minimal therapeutically beneficial dose that is less than the toxic dose of an active agent. On the other hand, a therapeutically effective amount of an antibody of the disclosure is an amount that reduces the biological activity of PD-1 in mammals, preferably humans.

The route of administration of an antibody of the disclosure can be oral, parenteral, inhalation or local. Preferably antibodies of the disclosure can be involved in a pharmaceutical composition acceptable for parenteral administration. The term "parenteral" as used herein includes intravenous, intramuscular, subcutaneous, rectal, vaginal or intraperitoneal administration. Intravenous, intraperitoneal or subcutaneous injections are preferred routes of administration. Acceptable pharmaceutical carriers for such injections are well known from the prior art.

As described in appropriate guidelines, pharmaceutical compositions shall be sterile and stable under the conditions of production and storage in a container, which is provided by, for example, hermetically sealed vials (ampoules) or syringes. Thus, pharmaceutical compositions can be subjected to filtration sterilization after preparing the composition, or can be made microbiologically suitable by any other technique. A typical composition for an intravenous infusion can include 250-1000 ml of fluid such as sterile Ringer's solution, physiologic saline, dextrose solution or Hank's salt solution, and a therapeutically effective dose (for example, 1-100 mg/ml or more) of an antibody concentrate. Doses may vary depending on disease type and severity. It is well known from the state of the medical art that doses for a patient depends on multiple factors including patient's sizes, body surface area, age, specific compound to be administered, gender, duration and route of administration, general health state and other simultaneously administered medications. A typical dose can be, for example, in a range of 0.001-1000 µg; however, doses lower and higher than this illustrative range are anticipated, especially given the above-mentioned parameters. The daily parenteral dosing regimen may be from 0.1 µg/kg to 100 µg/kg of overall body weight, preferably from 0.3 µg/kg to 10 µg/kg, and more preferably from 1 µg/kg to 1 µg/kg, even more preferably from 0.5 to 10 µg/kg of body weight per day. The treatment process can be monitored by periodical assessment of patient's health state. For repeated administration for several days or longer, depending on patient's condition, the treatment is repeated until the desired response or suppression of symptoms of a disease. However, another dosing regimens not described herein can also be applied. The desired dose may be administered by single bolus or multiple bolus dosing, or by means of a continuous infusion of an antibody depending on a pharmacokinetic breakdown desired by a practitioner.

Said assumed properties of an antibody largely depend on a physician's decision. The intended effect is the key factor for choosing a proper dose and regimen. Factors considered herein include a certain disease to be treated, a certain mammal to receive the treatment, clinical condition of a certain patient, disorder cause, antibody administration site, specific antibody type, route of administration, administration regimen and other factors well known in the medical arts.

Therapeutic agents of the disclosure can be frozen or lyophilized and reconstituted in an appropriate sterile carrier prior to administration. Freeze-drying and reconstitution can result in some loss of antibody's activity. Doses can be adjusted to compensate this loss. In general, pharmaceutical composition pH values from 6 to 8 are preferable.

Therapeutic use of a binding molecule of the disclosure

In one aspect, a binding molecule of the disclosure is useful in the treatment of disorders that are associated with PD1 activity.

"Treat", "treating" and "treatment" refer to a method of alleviating or abrogating a biological disorder and/or at least one of attendant symptoms thereof. As used herein, to "alleviate" a disease, disorder or condition means reducing the severity and/or occurrence frequency of the symptoms of a disease, disorder, or condition. Further, references herein to "treatment" include references to curative, palliative and prophylactic treatment.

In one aspect, the subject is a mammal, preferably a human subject. Said subject may be either male or female, of any age.

"Therapeutically effective amount" is intended to refer to that amount of the therapeutic agent being administered which will relieve to some extent one or more of the symptoms of the disorder being treated.

The binding molecules of the disclosure may be administered alone or in combination with one or more other preparations or antibodies (or any combination thereof). Thus, the pharmaceutical compositions, methods and uses of the disclosure also encompass embodiments of combinations (co-administration) with other active agents, as described below.

As used herein, the terms "co-administration", "co-administered" and "in combination with", referring to binding molecules and one or more other therapeutic agents, are expected to mean, refer to or include the following:

simultaneous administration of such combination of a binding molecule of the disclosure and a therapeutic agent to a patient in need of treatment, when such components are formulated together into a single dosage form which releases said components at substantially the same time to said patient, substantially simultaneous administration of such combination of a binding molecule of the disclosure and a therapeutic agent to a patient in need of treatment, when such components are formulated apart from each other into separate dosage forms which are taken at substantially the same time by said patient, whereupon said components are released at substantially the same time to said patient, sequential administration of such combination of a binding molecule of the disclosure and a therapeutic agent to a patient in need of treatment, when such components are formulated apart from each other into separate dosage forms which are taken at consecutive times by said patient with a significant time interval between each administration, whereupon said components are released at substantially different times to said patient; and sequential administration of such combination of a binding molecule of the disclosure and a therapeutic agent to a patient in need of treatment, when such components are formulated together into a single dosage form which releases said components in a controlled manner, whereupon they are concurrently, consecutively, or jointly released at the same and/or different times to said patient, where each portion may be administered by either the same or different routes.

The binding molecules of the disclosure can be administered without further therapeutic treatment, i.e., as an independent therapy. Furthermore, treatment by the binding molecules of the disclosure may comprise at least one additional therapeutic treatment (combination therapy). In some embodiments, the binding molecule may be administered jointly or formulated with another medication/preparation for the treatment of an autoimmune or inflammatory disease.

Pharmaceutical preparations comprising a binding molecule of the present disclosure and at least one other agent (e.g., an immunosuppressive or anti-inflammatory agent) may be used as a combination therapy for simultaneous, independent or consecutive administration in the treatment of inflammatory and autoimmune disorders.

It is meant that the binding molecules of the disclosure may be used in the methods of treatment as described above, may be used in the treatment as described above, and/or may be used in the manufacture of a medication for treatment as described above.

Doses and Routes of Administration

Any method for administering peptides, proteins or antibodies accepted in the art may be suitably employed for a binding molecule of the disclosure.

The pharmaceutical compositions of the disclosure are typically suitable for parenteral administration. As used herein, "parenteral administration" of a pharmaceutical composition includes any route of administration characterized by physical breaching of the tissue of a subject and administration of a pharmaceutical composition through the breach in the tissue, thus generally resulting in the direct administration into the blood stream, into the muscle, or into an internal organ. Thus, parenteral administration includes, inter alia, administration of a pharmaceutical composition by virtue of injection of the composition, by administration of the composition through a surgical incision, by application of the composition through a tissue-penetrating non-surgical wound, and the like. In particular, parenteral administration is meant to include, inter alia, subcutaneous, intraperitoneal, intramuscular, intrasternal, intravenous, intraarterial, intrathecal, intraventricular, intraurethral, intracranial, intrasynovial injection or infusions; and kidney dialytic infusion techniques. Intra-tumor delivery, for example, intra-tumor injection, can also be useful. Regional perfusion is also provided. Preferred embodiments include intravenous and subcutaneous routes.

Dosage forms of pharmaceutical compositions suitable for parenteral administration typically comprise an active ingredient combined with a pharmaceutically acceptable carrier, such as sterile water or sterile isotonic saline. Such dosage forms may be prepared, packaged, or sold in a form suitable for bolus administration or for continuous administration. Injectable formulations may be prepared, packaged, or sold in a common dosage form, e.g., in ampoules or in multi-dose containers containing a preservative. Formulations for parenteral administration include, inter alia, suspensions, solutions, emulsions in oily or aqueous bases, pastes, and the like. Such dosage forms may further comprise one or more additional ingredients including, inter alia, suspending, stabilizing, or dispersing agents. In one embodiment, a composition for parenteral administration comprises an active ingredient which is provided in dry (i.e. powder or granular) form for reconstitution with a suitable base (e.g., sterile pyrogen-free water) prior to parenteral administration of the reconstituted composition. Parenteral dosage forms also include aqueous solutions which may comprise excipients such as salts, carbohydrates and buffering agents (preferably to pH 3 to 9), but, for some applications, they may be more suitably formulated as a sterile non-aqueous solution or as a dried form to be used in conjunction with a suitable base such as sterile pyrogen-free water. Exemplary forms for parenteral administration include solutions or suspensions in sterile aqueous solutions, for example, aqueous propylene glycol or dextrose solutions. Such dosage forms can be buffered, if necessary. Other suitable dosage forms for parenteral administration may include those which comprise an active ingredient in a microcrystalline form, or in a liposomal preparation. Dosage forms for parenteral administration may be formulated to have an immediate and/or modified release. Modified release dosage forms include a delayed, sustained, pulsed, controlled, targeted and programmed release.

For example, in one aspect, sterile injectable solutions can be prepared by incorporating at least one binding molecule in the required amount in an appropriate solvent with one ingredient or a combination of ingredients enumerated above, as required, followed by filtered sterilization. Dispersions are typically prepared by incorporating the active compound into a sterile solvent that contains a basic dispersion medium and the other required ingredients from those enumerated above. In the case of sterile powders for the preparation of sterile injectable solutions, the methods for preparation are freeze-drying (lyophilization) that yields the powder of an active ingredient plus any additional desired ingredient from a previously sterile-filtered solution thereof. The proper fluidity of a solution can be maintained, for example, by the use of a coating such as lecithin, by the maintenance of a required particle size in the case of dispersions and by the use of surfactants. Prolonged absorption of injectable compositions can be brought about by virtue of incorporating in the composition an agent that delays absorption, for example, monostearates and gelatin, and/or by virtue of modified release coatings (e.g., slow release coatings).

The binding molecules of the disclosure can also be administered intranasally or by inhalation, typically in the form of a dry powder (either alone, as a mixture, or as particles comprising mixed components, for example, mixed with a suitable pharmaceutically acceptable excipient) from a dry powder inhaler, such as a pressurized aerosol container, pump, spray, atomizer (preferably an atomizer using electrohydrodynamics to produce fine mist), or nebulizer, wherein a suitable propellant is used or not used, or as nasal drops.

A pressurized container, pump, spray, atomizer, or nebulizer typically contains a solution or suspension of a binding molecule of the disclosure comprising, for example, a suitable agent for dispersing, reconstituting, or extending release of the active substance, a propellant as solvent.

Prior to use as a dry powder or suspension, the medicinal preparation is typically micronized to a size suitable for delivery by virtue of inhalation (typically less than 5 microns). This may be achieved by virtue of any suitable comminuting technique, such as spiral jet milling, fluid bed jet milling, supercritical fluid processing to form nanoparticles, high-pressure homogenization, or spray drying.

Capsules, blisters and cartridges for use in an inhaler or insufflator may be formulated to contain a powder mix of a compound of the disclosure, a suitable powder base and performance modifier.

A suitable solution formulation for use in an atomizer using electrohydrodynamics to produce a fine mist may contain a suitable dose of a binding molecule of the disclosure per actuation and the actuation volume may vary from, e.g., 1 μl to 100 μl.

Suitable flavours, such as menthol and levomenthol, or sweeteners, such as saccharin or saccharin sodium, may be added to those dosage forms of the disclosure intended for inhalation/intranasal administration.

Dosage forms for parenteral administration may be formulated for an immediate and/or modified release. Modified release dosage forms include a delayed, sustained, pulsed, controlled, targeted and programmed release.

In the case of dry powder inhalers and aerosols, the dosage unit is determined by means of a valve which delivers a metered amount. Units in accordance with the disclosure are typically arranged to administer a metered dose or "puff" of a binding molecule of the disclosure. The overall daily dose will typically be administered in a single dose or, more frequently, as divided doses throughout the day.

The binding molecules of the disclosure may also be formulated as dosage forms for peroral administration. Peroral administration may include swallowing, so that the compound enters the gastrointestinal tract, and/or buccal, lingual, or sublingual administration by which the compound enters the blood stream directly from the mouth.

Dosage forms suitable for peroral administration include solid, semi-solid and liquid systems such as tablets; soft or hard capsules comprising multi- or nano-particulates, liquids, or powders; lozenges (including liquid-filled); chews; gels; fast dispersing dosage forms; films; ovules; sprays; and buccal/mucoadhesive patches.

Liquid dosage forms include suspensions, solutions, syrups and elixirs. Such dosage forms may be employed as excipients in soft or hard capsules (made, for example, of gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid dosage forms may also be prepared by reconstituting a solid substance, for example, from a sachet.

The binding molecules of the disclosure will be administered in an amount that is effective in treatment of the condition in question, i.e. in doses and during the periods of time required to achieve the desired result. A therapeutically effective amount may vary according to factors such as the specific condition to be treated, age, sex, and weight of a patient, and whether the binding molecules are administered alone or in combination with one or more additional anti-autoimmune or anti-inflammatory treatment techniques.

Dosage regimens may be adjusted to provide the optimum response. For example, a single bolus may be administered, several divided doses may be administered over time or the dose may be proportionally reduced or increased as indicated by the exigencies of the therapeutic situation. It is especially advantageous to formulate parenteral compositions in a unit dosage form for ease of administration and uniformity of dosage. A unit dosage form as used herein is intended to refer to physically discrete units suited as unitary dosages for patients/subjects to be treated; each unit contains a predetermined quantity of active compound calculated to produce the desired therapeutic effect in association with the desired pharmaceutical carrier. Specification for the unit dosage forms of the disclosure is typically dictated by and directly dependent on (a) the unique characteristics of a chemotherapeutic agent and particular therapeutic or prophylactic effect to be achieved, and (b) the limitations inherent in the art of compounding such an active compound for the treatment of sensitivity in the subjects.

Thus, a skilled artisan would appreciate, based upon the disclosure provided herein, that the doses and dosage regimen are adjusted in accordance with methods well known in the therapeutic arts. That is, the maximum tolerable dose can be readily established, and the effective amount providing a detectable therapeutic effect to a patient may also be determined, as can the temporal requirements for administering each agent to provide a detectable therapeutic effect to a patient. Thus, while certain dose and administration regimens are exemplified herein, these examples in no way limit the doses and administration regimen that may be provided to a patient in practicing the embodiments of the disclosure.

It is to be noted that dosage values may vary with the type and severity of the condition to be alleviated and may include single or multiple doses. Furthermore, it is to be understood that for any particular subject, specific dosage regimens should be adjusted over time according to the individual need and the judgment of a medical professional administering or supervising the administration of the compositions, and that dosage ranges set forth herein are exemplary only and are not intended to limit the scope or practice of the claimed compositions. Furthermore, the dosage regimen with the compositions of the present disclosure can be based on various factors, including the type of a disease, age, weight, gender, patient's health condition, severity of a condition, route of administration and a particular binding molecule used. Thus, the dosage regimen may widely vary, but can be determined regularly using standard techniques. For example, doses may be adjusted based on pharmacokinetic or pharmacodynamic parameters, which may include clinical effects such as toxic effects and/or laboratory values. Thus, the present disclosure encompasses individual dose escalation as determined by a skilled artisan. Methods for determining appropriate dosages and regimens are well known in the art and would be understood by a skilled artisan once provided the ideas disclosed herein.

Examples of suitable administration methods are provided above. It is believed that a suitable dose of a binding molecule of the disclosure will be in the range of 0.1-100 mg/kg, including about 0.5-50 mg/kg, for example about 1-20 mg/kg. A binding molecule may be administered, e.g., in a dose of at least 0.25 mg/kg, such as at least 0.5 mg/kg, including at least 1 mg/kg, e.g., at least 1, 5 mg/kg, such as at least 2 mg/kg, e.g., at least 3 mg/kg, including at least 4 mg/kg, e.g., at least 5 mg/kg; and for example up to a maximum of 50 mg/kg, including up to a maximum of 30 mg/kg, e.g., up to a maximum of 20 mg/kg, including up to a maximum of 15 mg/kg. The administration will typically be repeated in appropriate time intervals, such as once a week, once every two weeks, once every three weeks or once every four weeks, and for as long as deemed appropriate by a responsible physician, who may, in some cases, increase or reduce the dose if necessary.

Effective amount for the treatment of autoimmune or inflammatory disorders can be measured by the ability thereof to stabilize the progression of disease and/or to improve the symptoms in a patient, and preferably to reverse disease manifestations. The ability of a binding molecule of the disclosure to suppress autoimmune or inflammatory disorders can be evaluated in in vitro assays, for example as described in the given examples, as well as in suitable animal models that predict efficacy in such disorders. A suitable dosage regimen will be selected to provide an optimal therapeutic response in a certain situation, e.g., single bolus administration or continuous infusion with the possible adjustment of a dose as indicated by the exigencies of each case.

Diagnostic Use and Compositions

The binding molecules of the disclosure are also used in diagnostic processes (e.g., in vitro, ex vivo). For example, they can be used for detecting or measuring the level of PD-1 in samples obtained from a patient (e.g., tissue sample or a sample of body fluid, such as an inflammatory exudate, blood, serum, intestinal fluid, saliva or urine). Suitable methods for detection and measurement include immunoassays, such as flow cytometry, enzyme-linked immunosorbent assay (ELISA), chemiluminescent assay, radioimmunoassay, and immunohistology.

Articles of Manufacture

In another embodiment, an article of manufacture is provided containing materials useful for the treatment or prevention of disorders and conditions described above.

The article of manufacture comprises a container with an antibody-containing pharmaceutical composition with a label, and possibly a package insert. Suitable containers include, e.g., vials, ampoules, syringes and analytical tubes. The containers may be made of a plurality of materials such as glass or polymer material. The container comprises a composition of the disclosure which is effective for treating a PD-1-mediated disease or disorder and can have a sterile access port (e.g., the container may be an intravenous solution bag or a vial having a stopper pierceable by a hypodermic injection needle). An anti-PD-1-antibody of the disclosure is an active agent of the composition. A label located on the container or a package insert attached thereto indicates that the composition is used for treating the desired disease. The article of manufacture may further comprise a second container with a pharmaceutically acceptable buffer such as phosphate-buffered saline, Ringer's solution and dextrose solution. It can further include other materials desirable from a commercial and consumer standpoint, including other buffers, diluents, filters, needles, syringes and package inserts.

The following examples are provided to better understand the disclosure. These examples are presented for illustrative purposes only and are not intended to limit the scope of the present disclosure in any way.

EXAMPLES

Example 1

Engineering of a Naive Human Antibody Fab-Library MeganLib™

Total RNA of B lymphocytes from blood samples of more than one thousand individual human donors was isolated using RNeasy Mini Kit according to the suggested protocol (QIAGEN). An RNA concentration assay was performed using Nanovue kit (GE Healthcare); the quality of isolated RNA was tested by means of 1.5% agarose gel electrophoresis.

A reverse transcription reaction was conducted using MMLV RT kit (Evrogen) according to the recommended protocol with MMuLV reverse transcriptase and random hexamer oligonucleotides as primers.

Reverse transcription products were used as a matrix in a two-stage polymerase chain reaction to obtain the genes of variable domains flanked with restriction sites; the reaction was performed using oligonucleotide kit and protocols by [J Biol Chem. 1999 Jun. 25; 274(26): 18218-30].

Figure 2A:
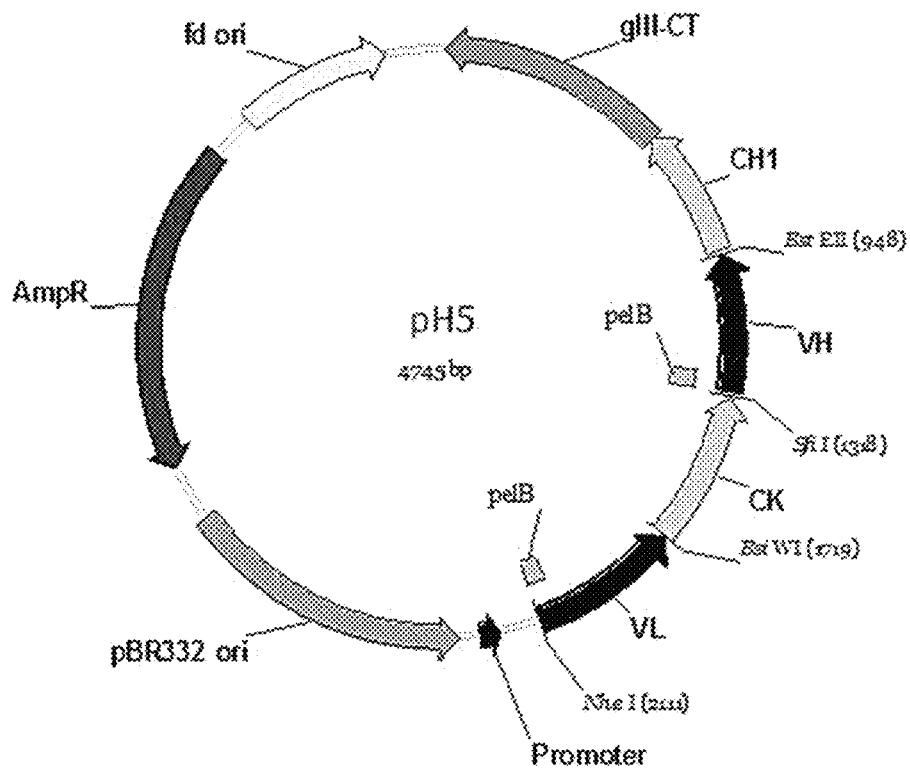
FIG. 2. Phagemid for cloning of Fab phage display libraries (A) and expression plasmid for production of Fab (B).

The obtained DNA preparation VL-CK-VH (FIG. 1) was treated with NheI/Eco91I restriction endonucleases and ligated into original phagemid pH5 (FIG. 2A). Ligation products were transformed into SS320 electrocompetent cells prepared in accordance with protocols [Methods Enzymol. 2000; 328: 333-63.]. The repertoire of combinatorial phage Fab-display library MeganLib™ was $10^{11}$ transformants. The preparations of phage-Fab-libraries were prepared in accordance with the earlier described procedure [J Mol Biol. 1991 Dec. 5; 222(3): 581-97].

Example 2

Selection of Fab-Libraries of Phage Antibodies

Figure 2B:
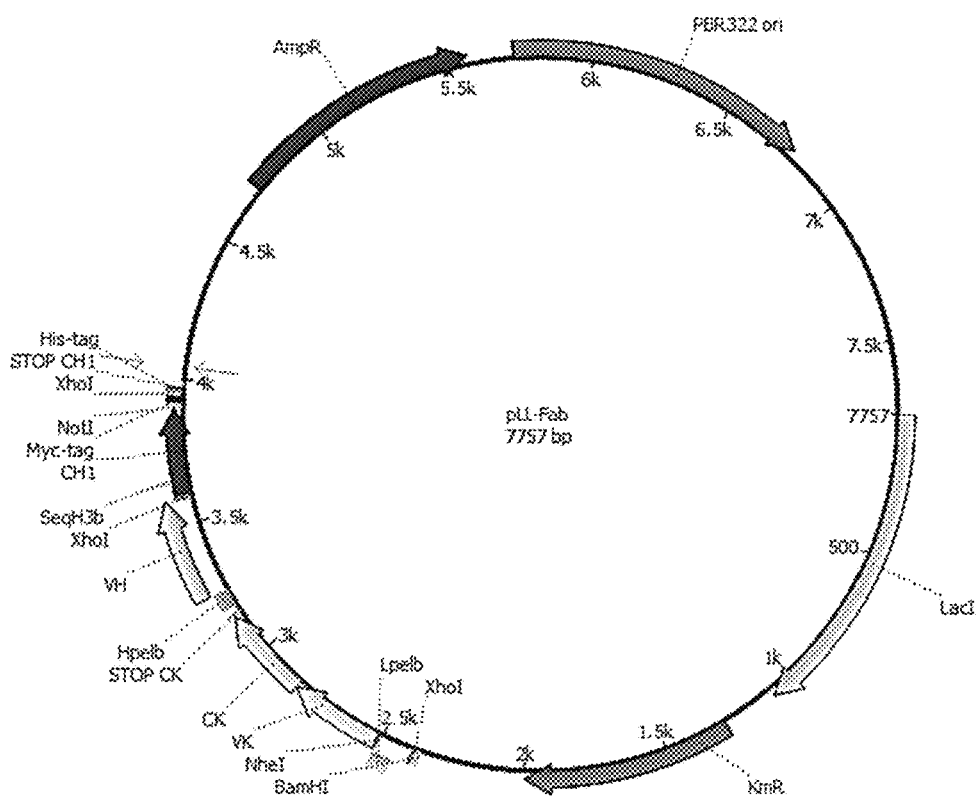

Specific anti-PD-1 phage Fab-antibodies were isolated from a combinatorial library phage Fab-display library of MeganLib™. Selection was performed using a recombinant human PD-1, with panning under conditions as described earlier (J Biol Chem. 1999 Jun. 25; 274(26): 18218-30; Nat Biotechnol. 1996 March; 14(3):309-14; J Mol Biol. 1991 Dec. 5; 222(3): 581-97). To perform the selection process by the panning method, human PD-1 in 50 mM carbonate buffer (pH 9.5) was adsorbed overnight at 4° C. on the surface of HighSorb tubes (Nunc). Further, tubes were washed with PBS (pH 7.4) and then blocked with a solution containing PBS (pH 7.4)—fat-free milk (0.5% weight/volume) for 1 hour. Then, 2-4 ml of phage solution ($10^{13}$ phage particles per ml) in PBS (pH 7.4)—fat free milk (0.5% w/vol) were transferred to the tube with the antigen, and the system was incubated for 1 hour under stirring. Unbound phages were removed by a series of washing cycles with PBS (pH 7.4)—Tween 20 (0.1% vol./vol.). The number of washing cycles was increased from the first round to the third one—20-30-40 times, respectively. Phage particles that remained bound were eluted with 100 mM Gly-HCl solution (pH 2.5) during 15 min under stirring, and then neutralized with 1 M TRIS-HCl (pH 7.6). *E. coli* TG1 bacteria were infected with phages obtained; further, phages were isolated and used in the next selection cycle. After the second and third round of selection, DNA (phagemids) were isolated and genes of antibody variable domains were cloned to expression vectors (FIG. 2B) for production of Fab in *E. coli*. cells.

Example 3

Analysis of Fab Specific Binding to Human PD-1

ELISA was used to measure the binding of test Fab-fragments to human PD-1. Fab with a published Nivolumab sequence (Bristol-Myers Squibb) was used as a positive control. In order to analyze the specific binding, ELISA plate wells (medium binding from Greiner bio one) were coated with 50 µl (0.5 µg/ml in 1× coating carbonate buffer, pH 9.5) PD1-H6F, hermetically closed and incubated overnight at 4° C. All further stages were conducted in accordance with the standard ELISA protocol with a high-performance automated platform based on robotic systems such as Genetix Qpix2xt (Molecular Devices) and Tecan Freedom EVO 200 (Tecan). Non-specific binding was blocked by adding a blocking buffer BB (200 µl 0.5% fat-free milk in PBS). Plates were incubated on a shaker for 1 h at room temperature. After washing with PBS-Tween, each cell was coated with 50 µl of test Fab-containing cell supernatant mixed with the equal volume of BB. Plates were incubated on a shaker for 1 hour at room temperature; further, each plate well was 3 times washed with PBS-Tween buffer. After washing, each well was coated (50 µl/well) with anti-human Fab HRP-conjugated secondary antibody (Pierce-ThermoScientific) in PBS-Tween (1:5000). Plates were transferred to rotation shaker (50 min at room temperature) and then 3 times washed with PBS-Tween buffer as described above. Colorimetric signal was obtained by adding TMB (50 µl/well) until saturated (average of 3-5 min); further color development was blocked by adding the stop solution (30 µl/well, 10% sulfuric acid). Absorbance was measured at 450 nm using an appropriate Tecan-Sunrise plate reader (Tecan). Antibody binding was proportional to the signal produced.

Example 4

Competitive ELISA of blocking the interaction of PDL1 ligand and PD-1 receptor

A competitive ELISA technique was used to test the antagonistic capacity of previously selected anti-PD-1 specific Fab. Fab with published Nivolumab sequence (Bristol-Myers Squibb) was used as a positive antagonist control. ELISA well plates (medium binding, Greiner bio one) were covered with 50 µl/well PD1-H6F receptor (1 µg/ml solution in 1× coating carbonate buffer pH 9.5) and incubated overnight at 4° C. All further stages were performed in accordance with standard ELISA protocols with a high-performance automated platform based on robotic systems such as Genetix Qpix2xt (Molecular Devices) and Tecan Freedom EVO 200 (Tecan). Non-specific binding was blocked by adding a blocking buffer BB (200 μl 0.5% fat-free milk in PBS). Plates were incubated on a shaker for 1 h at room temperature.

After the plate containing PD1 receptor was washed of BB solution, it was coated with the test Fab-containing cell supernatant, incubated under 500 rpm shaking for 45 min at room temperature. Then it was mixed with 50 μl PDL1-Fc at a final concentration of 1 μg/ml, and incubated for 45 min under the same conditions, further, each plate well was washed 3 times with PBS-Tween buffer. Further, 50 μl/well of goat anti-human IgG (Fc) HRP-conjugated secondary antibody (Sigma) were added in PBS-Tween (1:5000). Plates were incubated on rotation shaker for 45 min at room temperature and 5 times washed with PBS-Tween, as mentioned above. A colorimetric signal was obtained by adding TMB (50 μl/well) until saturated (average of 3-5 min); further color development was blocked by adding the stop solution (30 μl/well, 10% sulfuric acid). Absorbance was measured at 450 nm using an appropriate Tecan-Sunrise plate reader (Tecan). Fab binding was inversely proportional to the colour signal produced.

Example 5

Comparative koff-Screening for Anti-PD1 Fab Human Candidates koff screening was performed using Pall Forte Bio Octet Red 96. Anti-FABCH1 biosensors were rehydrated for 30 min in a working buffer comprising 10 mM PBS (pH 7.2-7.4), 0.1% Tween-20 and 0.1% BSA. 10× working buffer was added to test samples of E. coli supernatants up to 1× final concentration. Anti-FABCH1 biosensors were then steeped into E. coli supernatants containing Fab-fragments of candidate antibodies and incubated for 12 hours at a temperature of 4° C. Sensors were then transferred to wells with an analyte solution (PD-1, 30 μg/ml) to achieve antigen-antibody association (300 sec). After that, sensors were returned into wells with working buffer for further dissociation (300 sec). Used sensors were subject to regeneration after each test: they were placed three times into regenerating buffer (Gly-HCl, pH 1.7) and then could be used in further experiments. The curves obtained were analyzed using Octet Data Analysis (version 7.0) according to the standard procedure with 1:1 interaction model.

Example 6

Producing Recombinant Antigens and Antibodies in Suspension Mammal Cell Culture

Antibodies and antigens were generated in an established cell line obtained from Chinese hamster ovary cells (CHO-K1) according to published protocols [Biotechnol Bioeng. 2005 Sep. 20; 91(6):670-677, Liao Metal., 2004; Biotechnol Lett. 2006 June; 28(11):843-848; Biotechnol Bioeng. 2003 Nov. 5; 84(3):332-342]. Cells constitutively expressing the gene of EBNA1 protein (Epstein-Barrvirus nuclear antigen 1) were used. A suspension culture was conducted in flasks on orbital shaker using serum-free media from Life Technologies Corporation and in accordance with manufacturer's guidelines. For transient expression, cells in a concentration of $2*10^6$/ml were transfected by means of linear polyethyleneimine (PEI MAX, Polysciences). DNA/PEI ratio was 1:3-1:10. In 5-7 days after transfection, cell culture was centrifuged under 2000 g for 20 min and filtered through a 0.22 μm filter. Target proteins were isolated from culture liquid by affine HPLC.

A recombinant PD-1 protein containing 6 His amino acids in C-terminal region was isolated and purified from culture liquid on Profinity IMAC Ni-charged resin (Bio-Rad). Prior to purification procedures, $NiCl_2$ was added to culture liquid to a concentration of 1 mM. Then 5 ml of Profinity IMAC Ni-charged was added to culture liquid and mixed on a shaker for 1 h at room temperature. Sorbent was transferred to 5 ml Thermo scientific Polypropylene columns and washed with 5 column volumes of PBS to remove non-specifically bound components. Bound antigen was eluted with 0.3 M imidazole (pH 8) and 150 mM NaCl. Then the protein was dialyzed into PBS (pH 7.4) by means of SnakeSkin Dialysis Tubing technique, filtered (0.22 μm), transferred into tubes and stored at −70° C.

Recombinant PD1-Fc and PDL1-Fc proteins were isolated and purified from cell culture on a Protein A column for affine HPLC. Cleared culture liquid was passed through 5 ml HiTrap rProtein A Sepharose FF column (GE Healthcare) equilibrated with phosphate buffered saline (PBS, pH 7.4). Then the column was washed with 5 volumes of PBS to remove non-specific bound components. Bound antigen was eluted with 0.1 M glycine buffer (pH 8). The principal protein elution peak was collected and brought to neutral pH with 1 M Tris-buffer (pH 8). All stages were conducted under 110 cm/h flow rate. Then the protein was dialyzed into PBS (pH 7.4) by means of SnakeSkin Dialysis Tubing technique, filtered (0.22 μm), transferred into tubes and stored at −70° C.

Figure 3A:
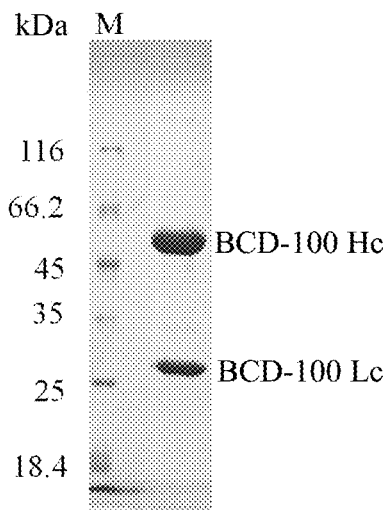
FIG. 3. BCD-100 electrophoregram under reducing conditions (3A, 12% SDS-PAGE), under non-reducing conditions (3B, 8% SDS-PAGE).
Figure 3B:
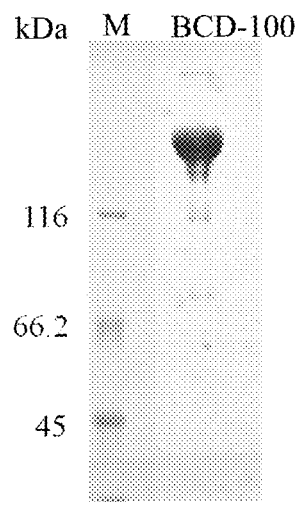

IgG1 antibodies were purified on a 1 ml Hi Trap rProteinA FF column (GE Healthcare) in accordance with the aforementioned procedure for PD1-Fc antigen. Purity of the obtained protein was evaluated by SDS-PAGE (FIGS. 3A and 3B).

Example 7

Reactivating NFAT-Signaling by Anti-PDI Antibodies in Jurkat-NFAT-PD1 Reporter Cell Line Engineering of a human T-cell line of Jurkat origin was conducted by introducing two genetic constructs into the genome thereof. One construct encodes a human PD1 receptor gene. The second construct encodes luc2P luciferase gene under control of NFAT-sensitive genetic element. The result was a reporter cell line Jurkat-PD1-NFAT-Luc2, which expresses PD1 receptor on the surface membrane and contains NFAT-dependent promoter that directs transcription of luc2P luciferase gene. Synthesis of the luciferase enzyme in cells of this line is proportional to the level of NFAT activity, which, in turn, reflects the overall level of cell activation.

Interaction of PDL1 with PD1 inhibits signaling from TCR receptors to NFAT-promoter. When anti-PDI Antibodies uncouple PDL1-PD1 interaction, reactivation of intracellular signaling occurs.

A plate for the experiment was prepared one day prior to analysis as follows: solution of anti-CD3 antibodies in PBS (1 μg/ml with 5 μg/ml PDL1-Fc) was introduced to 96-well opaque plate made of opaque plastic. Solution of anti-CD3 antibodies without PDL1 was used for a positive control of activation. Then, it was left overnight at +4° C.

Test antibodies were then diluted from 11 μg/ml in cell growth medium, using three-fold dilution, to fit ten-point curve, cells with antibody dilutions were incubated for 20 minutes at room temperature, then cells with antibodies were introduced to a prepared plate. A solution of anti-CD28 antibodies in growth medium was added to all wells to a final concentration of 0.25 µg/ml. Then it was left in a $CO_2$ incubator for 6 hours.

Figure 5:
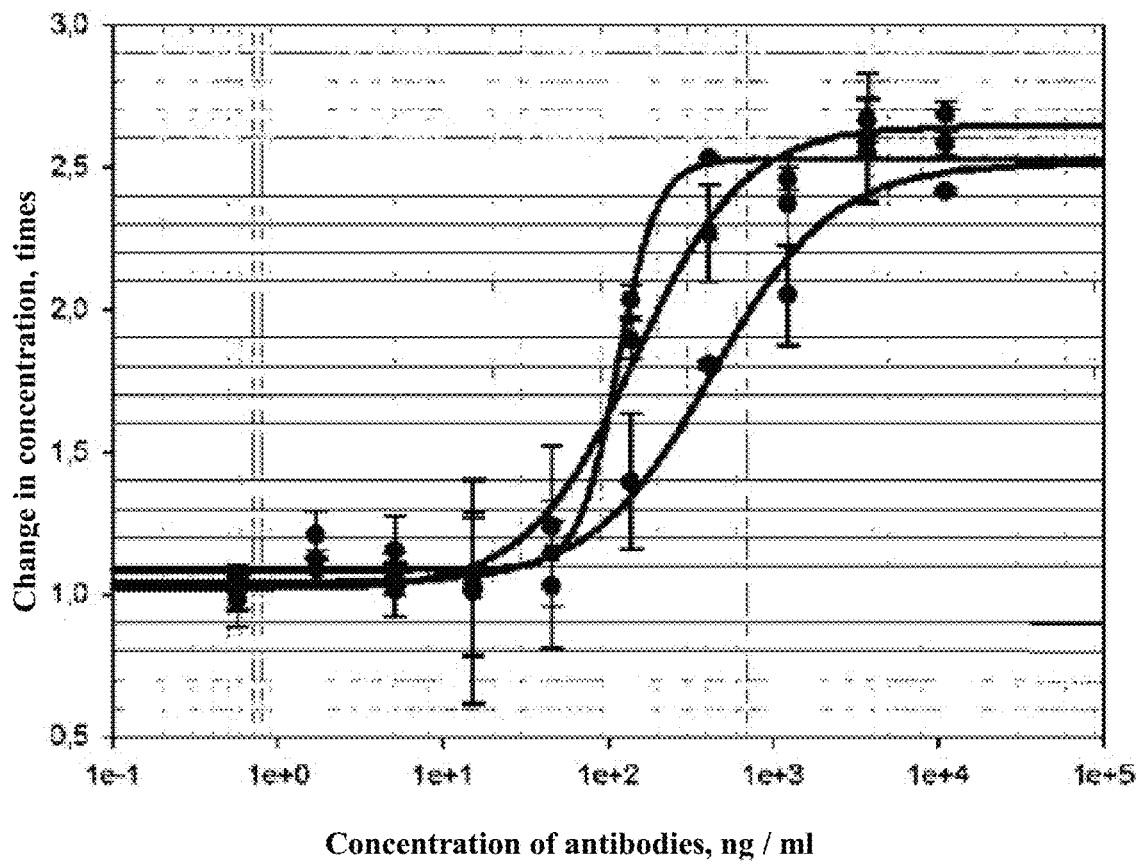
FIG. 5. Reactivation of NFAT-signaling by anti-PDI antibodies in Jurkat-NFAT-PD1 reporter cell line.

A luciferase substrate from Bio-Glo Luciferase assay system (Promega) pre-prepared according to protocol was thawed from −70° C. and added at a rate of V cells/V substrate. Luminescence was measured using Fluoroscan Ascent (FIG. 5). The anti-PD1 antibodies reactivate luminescence level in Jurkat-PD1-NFAT reporter line, and therefore bind to the receptor and inhibit PDL1/PD1 interaction. BCD-100 showed the best results, the effective dose (ED50) was 114.6 ng/µL.

Example 8

Stimulation of Production of IL-2 by Anti-PD1 Antibodies in Human whole Blood in the Presence of Staphylococcal Enterotoxin Superantigens, such as SEB cytotoxin (staphylococcal enterotoxin), activate T cells by virtue of binding a class II MHC molecule on antigen-presenting cells to TCR receptor Vβ element, resulting in production of cytokines, including IL2 autocrine growth factor.

The test is based on the description of an article (MK-3475; Anti-PD-1 Monoclonal Antibody) in Patients With Advanced Solid Tumors (Clin Cancer Res Published OnlineFirst May 14, 2015).

Briefly, whole blood was incubated with SEB or with SEB plus anti-PD1 antibodies, then IL-2 concentration was measured.

Figure 6:
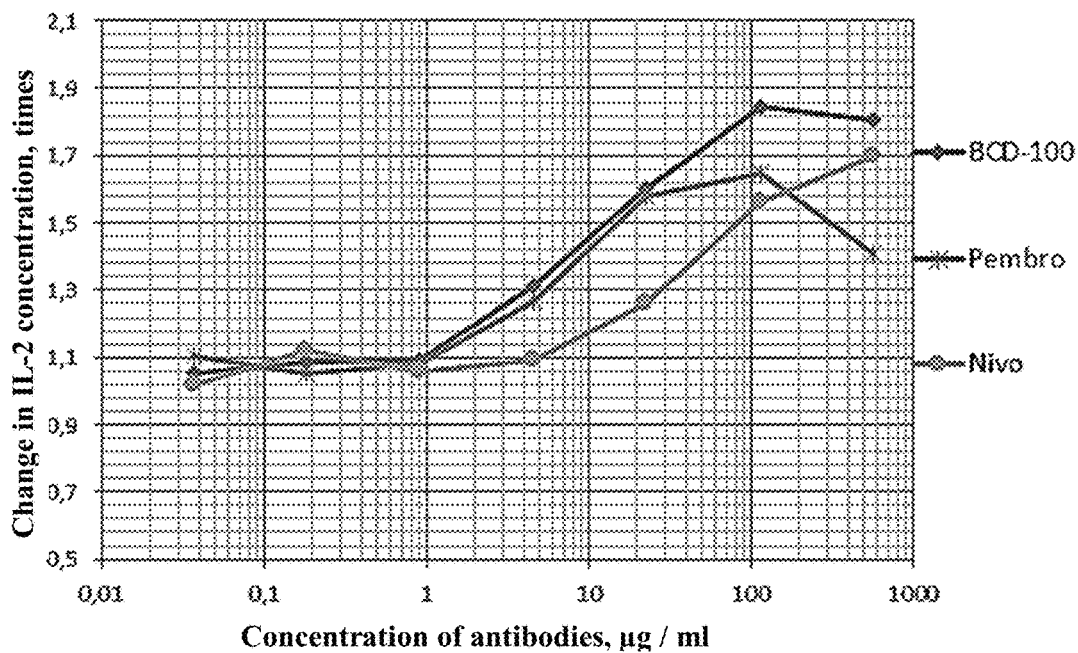
FIG. 6. Stimulation of production of IL-2 by anti-PD1 antibodies in human whole blood in the presence of staphylococcal enterotoxin.

Heparinized whole blood from donor was diluted 1:5 times in growth medium (RPMI with 10% fetal bovine serum). SEB was added to diluted blood to a final concentration of 1 µg/ml. Anti-PD1 antibodies were diluted in growth medium from 50 µg/ml with an increment of 3, totaling eight dilutions. A solution of blood and SEB in growth medium (volume/volume) was added to the diluted antibodies. Plates were incubated for 3 days in a $CO_2$ incubator at 37° C. Further, IL-2 concentration was measured in selected samples by ELISA technique (FIG. 6), according to a commercially available kit (Human IL-2 Quantikine ELISA Kit from R & D Systems) protocol. BCD-100 showed the best results due to greater functional activity than control antibodies.

Example 9

Analysis of Antibody-Dependent Cell-Mediated Cytotoxicity (ADCC) of Anti-PD1 Antibodies on Jurkat-PD1 Cell Line Grown Jurkat-PD1 cell culture intended for use in a quantitative test was collected from vials and centrifuged for 5 minutes at 200 g. Supernatant was drained and washed once again in a medium for a quantitative test.

The cell pellet was suspended in 5 ml of medium for the quantitative test; viability and number of cells were determined. Cell suspension was prepared for seeding white 96-well culture plates at $3 \times 10^5$ cells/ml.

Dilutions of the test sample were added to the wells of a 96-well plate. Jurkat-PD1 cell suspension was added to wells comprising test samples, and the plate was incubated for 15-30 minutes in a $CO_2$ incubator.

PBMCs cell suspension at a concentration of $7.5 \times 10^6$ cells/ml was prepared and added to wells comprising test samples. The plate was incubated at 37° C. in a $CO_2$ incubator for 4 hours.

Figure 7:
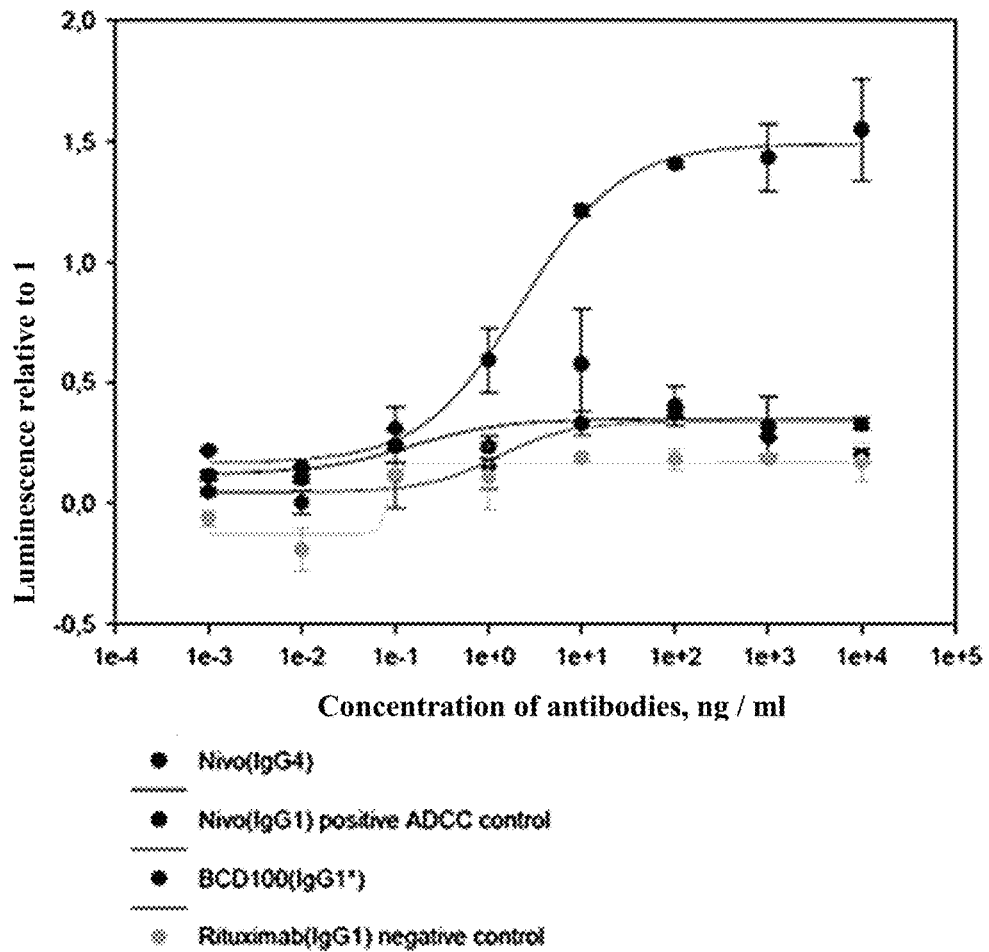
FIG. 7. Analysis of antibody-dependent cell-mediated cytotoxicity (ADCC) of anti-PD1 antibody on Jurkat-PD1 cell line.

Assay Buffer and AAF-Glo™ Substrate from CytoTox-Glo™ Cytotoxicity Assay kit were mixed and added to each well comprising test samples. A plate was incubated for 15 minutes at room temperature. Luminescence was measured using Fluoroscan Ascent FL (FIG. 7). A principle of the method is based on determining the activity of intracellular proteases, the resulting luminescence signal is proportional to the number of lysed cells. Anti-PD1 antibodies do not have detectable antibody-dependent cell-mediated cytotoxicity.

Example 10

Figure 4:
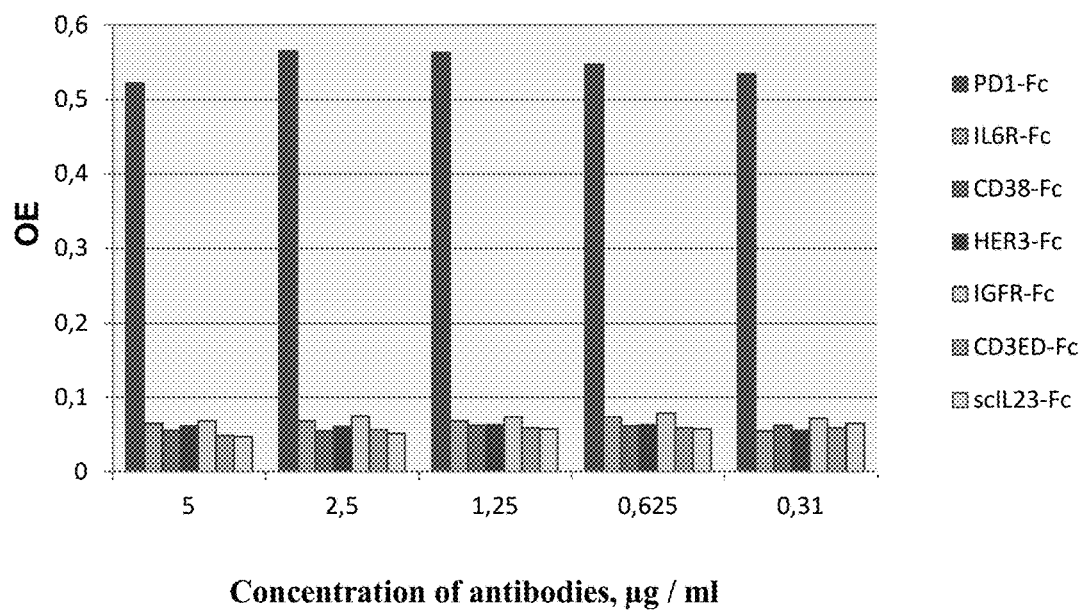
FIG. 4. Immunoenzymatic assay of interaction of BCD-100 with PD1 and other antigens.

Immunoenzymatic Aanalysis of Interaction of Anti-PD1 Antibodies with PD1 and Other Antigens ELISA was used to measure the relative affinity of antibodies to PD1 and other antigens. ELISA plate wells (medium binding from Greiner bio one) were used to measure the binding. ELISA plate wells were coated with 50 µl of PD1-Fc, IL6R-Fc, CD38-Fc, HER3-Fc, IGFR-Fc, CD3-Fc, IL23-Fc (1 µg/ml for PD1 and 5 µg/ml for the other antigens in 1× coating carbonate buffer), hermetically closed and incubated overnight at 4° C. All further stages were conducted in accordance with the standard ELISA protocol. Non-specific binding was blocked by adding a blocking buffer BB (200 µl 0.5% fat-free milk in PBS). Plates were incubated on a shaker for 1 h at room temperature. After washing with PBS-Tween, 50 µl per well of test antibodies were added at a concentration of 5 µg/ml in PBS-Tween. Plates were once again incubated, while shaken, for one hour at room temperature, thereafter each plate well was washed three times with PBS-Twin buffer. After washing, each well was coated (50 µl/well) with anti-human Fab HRP-conjugated secondary antibody (Pierce-ThermoScientific) in PBS-Tween (1:5000). Plates were transferred to a rotation shaker (50 min at room temperature) and then washed 3 times with PBS-Tween buffer as described above. A colorimetric signal was obtained by adding TMB (50 µl/well) until saturated (average of 3-5 min); further color development was blocked by adding the stop solution (30 µl/well, 10% sulfuric acid). Absorbance was measured at 450 nm using an appropriate Tecan-Sunrise plate reader (Tecan). Antibody binding was proportional to the signal produced (FIG. 4). Anti-PD1 antibody specifically binds to PD1 and does not bind to other antigens in question.

Example 11

Figure 9:
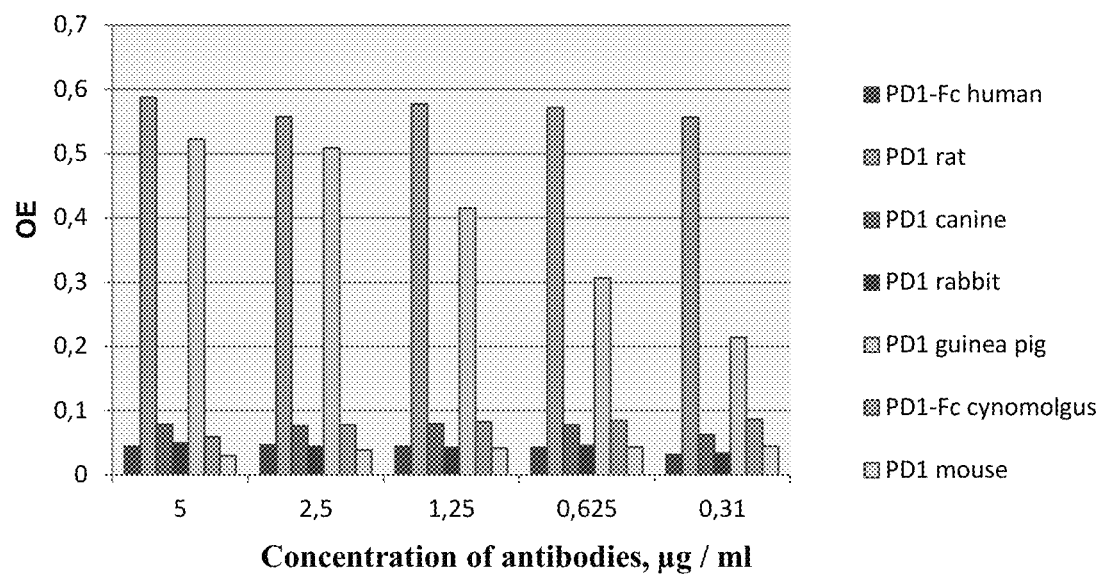
FIG. 9 Immunoenzymatic assay of interactions of BCD-100 with PD1 receptors of different organisms.

Immunoenzymatic Analysis of Interactions of Anti-PD1 Antibodies with PD1 Receptors of Different Organisms ELISA was used to measure relative affinity of antibodies to PD1 receptors of different organisms. ELISA plate wells (medium binding from Greiner bio one) were used to measure the binding. ELISA plate wells were coated with 50 µl of human and Javanese monkey PD1-Fc, PD1 of mouse, rat, dog, rabbit, guinea pig (0.5 µg/ml in 1× coating carbonate buffer, pH 9.5), hermetically closed and incubated overnight at 4° C. All further stages were conducted in accordance with the standard ELISA protocol. Anti-PD1 antibody specifically binds to human and cynomolgus monkey PD1 and does not bind to other test receptors (FIG. 9).

Example 12

Figure 10:
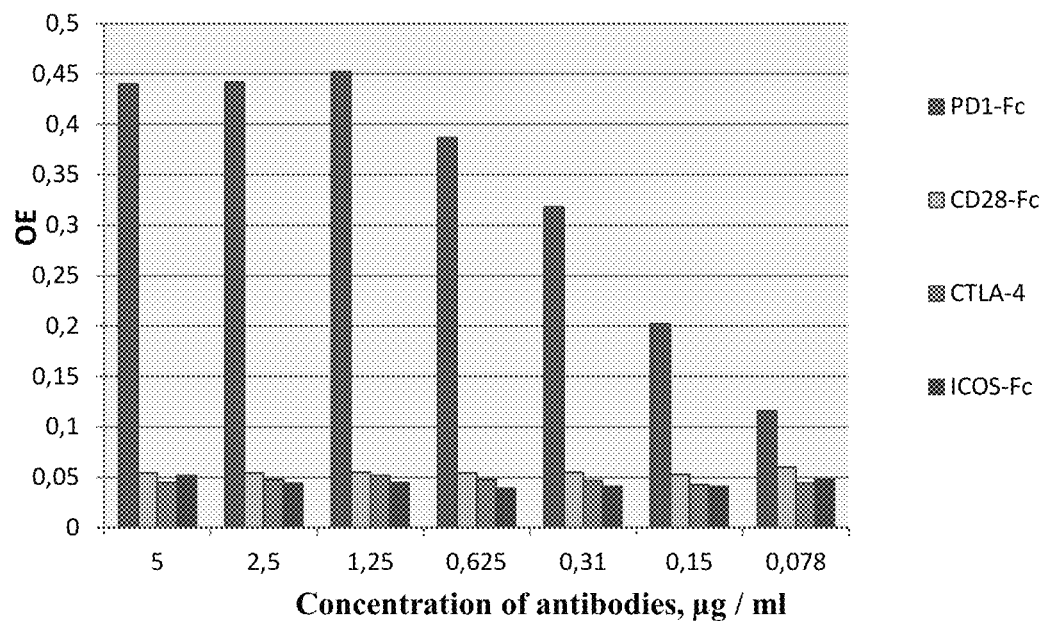
FIG. 10 Immunoenzymatic assay of interactions of BCD-100 with CD28 family receptors.

Immunoenzymatic Analysis of Interactions of Anti-PD1 Antibodies with CD28 Family Receptors ELISA was used to measure relative affinity of antibodies to CD28 family receptors ELISA plate wells (medium binding from Greiner bio one) were used to measure the binding. ELISA plate wells were coated with 50 µl of human PD1-Fc, CD28, CTLA-4 and ICOS-Fc (0.5 µg/ml in 1× coating carbonate buffer, pH 9.5), hermetically closed and incubated overnight at 4° C. All further stages were conducted in accordance with the standard ELISA protocol. Anti-PD1 antibody only binds to PD1 and does not bind to other CD28 family members (FIG. 10).

Example 13

Analysis of Interactions of Anti-PD1 Antibodies with Human and Cynomolgus Monkey PD1 Receptors on Octet RED 96

Affinity constants of an antibody binding to human and cynomolgus Monkey PD-1 was Investigated on OctetRed 96 (ForteBio). BCD100 antibodies were non-specifically immobilized on the surface of amine reactive second-generation sensors (ForteBio, Pall) according to the standard protocol described in the manufacturer's manual in regard to preparation and immobilization of AR2G sensors. An analysis was conducted at 30° C. using PBS comprising 0.1% Tween-20 and 0.1% BSA as a working buffer. Human and cynomolgus monkey PD-1 was titrated with working buffer from a concentration of 126 nM to 2 nM with an increment of 2.

Figures 11, 12:
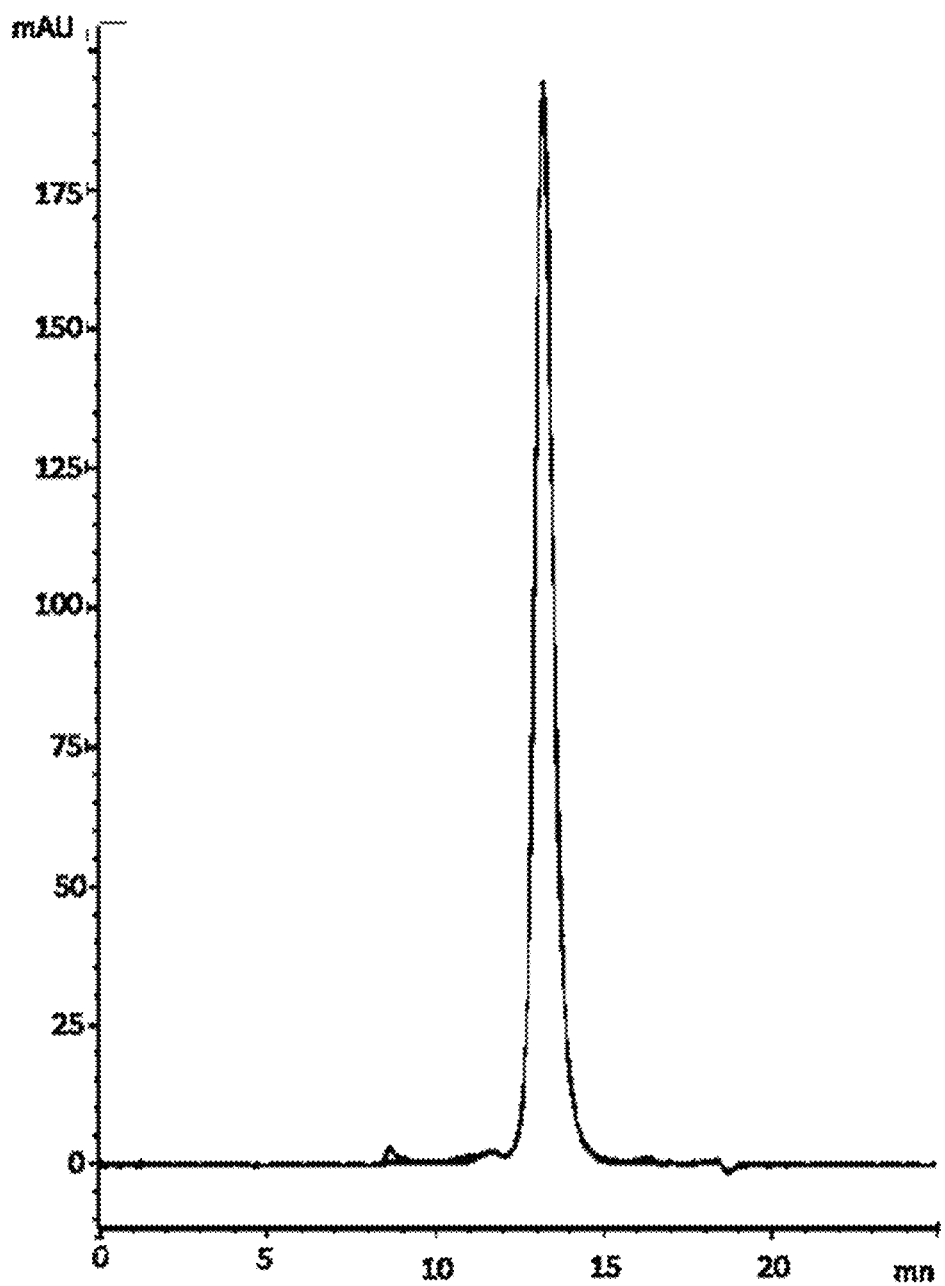
FIG. 11. Analysis of interactions of BCD-100 candidates with human and cynomolgus monkey PD1 receptors on Octet RED 96.
FIG. 12. Results of thermal stress (50° C., 12 h) of BCD-100 molecule.

Binding curves, after subtracting a reference signal, were analyzed using Octet Data Analysis software (Version 7.0) in accordance with the standard procedure and using 1:1 interaction model. Anti-PD1 antibody specifically binds to human and cynomolgus monkey PD1 antigen (FIG. 11).

Example 14

Analysis of Interactions of Anti-PD1 Antibodies with FcRn and Fcγ Receptors using Octet RED 96

Forte bio Octet RED96 and streptavidin (SA) biosensors were used to analyze the interaction of antibodies with FcgRIIIaV, FcgRIIaH, FcgRIIb, FcgRIa, FcRn.

In the course of experiment, biotin-labeled receptors were orientally immobilized on the surface of streptavidin-coated sensors. Antibodies were diluted in series from a concentration of 500 µg/ml with an increment of 2 by 7 points and placed in wells within a 96-well plate. Association stage was then carried out by virtue of immersing sensors in solutions of antibodies at various concentrations, further, dissociation stage was carried out by virtue of immersing sensors in a working buffer.

Working buffer PH7.4 was used to analyze antibody affinity to FcgRIIIaV, FcgRIIaH, FcgRIIb, FcgRIa, and working buffer PH6.0 was used to analyze affinity to FcRn.

The obtained curves, after subtracting a reference signal, were analyzed by SteadyState using 2:1 interaction model (heterogeneous ligand) in accordance with the standard procedure. The results are shown in FIG. 8. Analysis of affinity to Fcg receptors shows that effector functions of modified IgG1 are reduced and are approximately comparable to IgG4. Based on analysis of affinity to FcRn receptor, one can assume that pharmacokinetics of anti-PD1 antibody is identical to that of Nivolumab antibody.

Example 15

Determining Aggregation Stability of anti-PD1 Antibody Under Thermal Stress

BCD100 antibody preparation of 9 mg/ml in PBS buffer was heated for 12 hours at a temperature of 50° C. Aggregation after thermal stress was determined by high-performance gel-filtration chromatography. Chromatography was performed on a HPLC system (Agilent) on column Tosoh TSK-Gel G3000SWXL, 7.8 mm×30 cm, order no. 08541 with precolumn Tosoh TSKgel Guard SWXL, 6.0 mm×4.0 cm, with a particle diameter of 7 µm, order no. 08543. Elution was performed in isocratic mode, mobile phase: 50 mM NaFb, 0.3 M NaCl, pH 7.0 at a rate flow of 0.5 ml/min Detection was performed at wavelengths of 214 and 280 nm. Samples of antibodies were diluted with FSB buffer, pH 7.5, to a concentration of ~1 mg/ml. Injection volume was 10 microliters. Calibration mixture Gel filtration standard (Bio-Rad), order. no 151-1901. was pre-chromatographed. FIG. 12 shows combined chromatograms: red—intact, blue—after 12 h incubation at 50° C. Anti-PD-1 antibody remains stable under thermal stress (difference in aggregate content in solution before/after thermal stress was less than 5%).

Example 16

Engineering of a Stable Cell Line, Production and Purification of Anti-PD1 Antibody A stable cell line producing BCD-100 monoclonal antibody was obtained by transfecting with electroporation using Neon Transfection System (Life Technologies) the parental suspension CHO-S cell line with vector constructs that comprised the optimum ratio of light and heavy antibody chains. High level clonal lineages (over 1 g/l) were obtained using ClonePix robotic platform (Molecular Devices) and preliminary minipool selection stages using antibiotics in different cultivation formats. Productivity of selected clones was analyzed by Biomek FX robotics automated system (Beckman Coulter), and productivity was analyzed by Octet RED96 analytical system (Pall Life Sciences). DOE for selecting basic environment and cultivation scheme was carried out using Biomek FX robotics automated system (Beckman Coulter). Producer was cultured in serum-free media and feedings containing no animal-derived proteins.

Culture liquid was filtered through a Zeta Plus Maximizer 60M02» (3M) depth filter. Primary purification of the antibody was performed on Protein A affinity sorbent. The target protein was specifically eluted with glycine buffer pH 3.3-3.8 under acidic conditions. The collected eluate was exposed to acidic pH for 30-60 min for the purpose of viral inactivation, and then neutralized with 1M Tris-OH solution to pH 6.8-7.2. Final chromatographic purification to remove residual DNA, producer cell proteins, released affine sorbent's ligand, aggregates and antibody fragments was performed using CaptoAdhere sorbent (GE HealthCare Life-Sciences) in a flow-through mode. Thus, the protein solution was flowed through prepared sorbent pH 6.8-7.2, under low conductivity (<2 msec/cm$^2$). The purified protein was then subject to virus-removing filtration using Viresolve PRO filter kit (Millipore), concentrating and diafiltration against the final buffer containing histidine buffer (pH 6.0-6.5), Tween 80 and trehalose. Protein concentration was 50 mg/ml and higher.

Example 17

Obtaining of a Pharmaceutical Composition Comprising Anti-PD-1 Antibody of the Disclosure Antibody concentration to PD1 (BCD-100)—25 mg/ml, sodium acetate t/g—0.436 mg, mannitol—50 mg, Kolliphor (poloxamer) P188—0.2 mg, glacial acetic acid pH 5.15 Osm 300±20 mOsm until pH 5.0

Example 18

Study of Cross-Reactivity of Anti-PD1 Antibody in Normal Frozen Human Tissues

A study of cross-reactivity of anti-PD1 preparation was performed on normal frozen human tissues (autopsy material). The following 33 human tissues were used in the analysis: hypophysis, retina, stomach, peripheral blood cells, cerebral cortex, skin, lung, lymph node, uterus, tonsils, cerebellum, mammary gland, bladder, ureter, adrenal gland, peripheral nerve, parotid gland, liver, pancreas, striated muscle, kidney, prostate, spleen, heart, spinal cord, large intestine, small intestine, fallopian tube, thyroid and parathyroid glands, vascular endothelium, testis, ovary. Frozen suspension of Jurkat-PD1 cells comprising PD1 membrane antigen was used as a positive control.

Manufactured frozen tissue blocks from pieces of organ tissues were embedded in Tissue-Tec (Sacura) tissue-filling and freezing medium, frozen in liquid nitrogen vapor and stored at −70° C. Precipitated suspension of Jurkat-PD1 cells expressing PD1 were used as a positive control, $1*10^6$ cells/ml were resuspended in 1 ml of Tissue-Tec (Sacura) tissue-filling and freezing medium, resulting suspension was frozen in liquid nitrogen vapor, and stored at −70° C.

5 μm sections were prepared on Thermo HM525U cryostat. Further, sections were fixed with cold acetone for 10 minutes, dried in air at room temperature for 2-24 hours. Fixed sections were stored in the dark at −70° C.

Anti-PD1 preparation (JSC Biokad, Russia) was labeled with FITC using FluoReporter FITC Protein Labeling Kit (Invitrogen) according to the manufacturer's instructions.

Endogenous peroxidase was blocked. Sections were washed twice with PBS (0.05% Tween 20), endogenous peroxidase was blocked using Hydrogen Peroxide Block (Thermo) for 10 minutes at room temperature, and further washed twice with PBS.

Non-specific staining was blocked before the staining procedure as follows: sections were treated with Protein Block Serum-Free (Dako) for 10 minutes at room temperature. Primary antibodies were applied without washing.

Sections were coated with primary antibody at a working concentration of 0.2 μg/ml (anti-PD1 antibody labeled with FITC, human IgG1 isotype antibody at a concentration of 0.2 μg/ml) and incubated at room temperature for 1 hour, and then washed twice with PBS for 5 min each time.

A solution of murine monoclonal anti-FITC antibody conjugated to peroxidase (working dilution 1/1000) was incubated for 30 minutes at room temperature, and then washed twice with PBS for 5 min each time. Sections were treated with DAB staining solution for 10 minutes, and then washed twice with deionized water.

Nuclei were lightly stained with hematoxylin for 10 minutes, and then washed twice with deionized water. Sections were treated with 1% HCl solution for 1 second, and then three times washed with deionized water. Nuclei were stained with saturated lithium carbonate solution (blue) for 45 s. Once stained, sections were washed twice with deionized water, dehydrated in alcohol solutions with increasing concentration of alcohol (70%, 80%, 96%), clarified in a xylene replacer, embedded into mounting medium, and then cover-slipped using ClearVue (Thermo).

Semi-quantitative cytotoxic measurement of positive staining was performed. Screening of preparation was performed using Leica DM 6000B light microscope, and digital images were transmitted to a computer monitor via Leica DFC 420 video camera and recorded on a hard disk using included Leica Application Suite (version 2.5.0.R1). For screening, 40× lens was used, with a specific adjusted (digital setting) standard level of micropreparation illumination. Staining intensity in an image is proportional to relative concentration of labeled substance, in this case it is anti-PD1. In addition to visual assessment of immunopositive staining of cell types and structures, ImageJ digital image analysis software was used to measure the level of immunopositive staining in a selected area. Depending on staining intensity and total number of stained structures, evaluation was made using 0-3 point scale. Final immunopositive staining was evaluated taking into account intensity of staining of a tissue which was coated with control isotypic antibodies.

Example 19

Evaluation of In Vivo Efficacy of Anti-PD1 Antibody

Efficacy was evaluated by humanized PBMC mice (The Jackson Laboratory) which were injected subcutaneously with human melanoma cell line A2058. Each animal in the group received $2.5×10^6$ tumor cells. Cells were mixed with Matrigel® (1:1) prior to administration. The obtained mixture was administered subcutaneously. Efficacy was evaluated using three doses of BCD-100 preparation, Keytruda® reference preparation (positive control) and normal human immunoglobulin preparation for intravenous administration (negative control) (Table 1).

TABLE 1

Efficacy evaluation scheme

| Group | Animal qty | Preparation | Days | Method of administration | Dose, mg/kg |
|---|---|---|---|---|---|
| 1 | 6 (♂) | BCD-100 | 7, 10, 13, | i.p. | 5 |
| 2 | 6 (♂) | BCD-100 | 16, 19, 22, |  | 20 |
| 3 | 6 (♂) | BCD-100 | 25, 28 and |  | 40 |
| 4 | 6 (♂) | Keytruda ® (Pembrolizumab) Positive control | 31 |  | 40 |
| 5 | 6 (♂) | IVIg Vehivle vontrol |  |  | 40 |

In the course of the experiment, weight (before injection, and then twice a week) and volume of the tumor node in animals were evaluated using the following formula:

$$W^2 × L × 0.536,$$

where W—width of tumor node, L—length of tumor node. Animals were euthanized on day 37 of the experiment. Before euthanizing, the animal's blood was sampled to evaluate the level of circulating human blood lymphocytes of the following subpopulations:

CD45+CD20+ B-lymphocytes
CD45+CD3+ T-lymphacytes
CD45+CD3+CD4+ T-per cells
CD45+CD3+CD8+ Cytotoxic T Cells
CD45+CD3−CD(16+56)+ NK-cells Example 20

Anti-PD1 Antibody Toxicokinetic Evaluation

The below toxicokinetic study was carried out on cynomolgus monkeys using three BCD-100 dosage levels. A scheme for the experimental groups is shown in Table 2 below.

TABLE 2

Toxicokinetic study scheme

| Group no. | Animal qty | Preparation | Method of administration | Dose, mg/kg |
|---|---|---|---|---|
| 1 | 3 (♂) | Anti-PD-1 monoclonal antibody | intravenous | 10 |
| 2 | 3 (♂) | Anti-PD-1 monoclonal antibody | | 70 |
| 3 | 3 (♂) | Anti-PD-1 monoclonal antibody | | 140 |
| 4 | 3 (♂) | Placebo | | — |

The following parameters were evaluated during the study:

results of clinical examinations;

animal weight (before administration and on day 4, 8, 22, 42 of the experiment);

body temperature (before administration and after 1, 2, 4, 6, 24 hours after administration, on day 4, 8, 22, 42 of the experiment);

urinalysis (before administration and on day 4, 8, 22, 42 of the experiment);

complete blood analysis on the following parameters: number of erythrocytes, number of leucocytes, hemoglobin concentration (before administration and on day 4, 8, 22, 42 of the experiment);

biochemical analysis of serum on the following parameters: lactate dehydrogenase, total bilirubin, total protein, glucose, aspartate aminotransferase, alanine aminotransferase (before administration and on day 4, 8, 22, 42 of the experiment);

examination of concentration of preparation in the blood serum of primates (5, 15 minutes and 0.5, 1, 3, 6, 24, 30, 48, 72, 96, 120, 144, 168, 192, 264, 336, 408, 576, 888, 984 hours after administration).

Example 21

Evaluation of Toxicity in Case of Multiple Subcutaneous Administrations in Cynomolgus Monkeys for Three Months Followed by a Period without Administrations for Three Months Examination of toxicity in the case of multiple subcutaneous administrations for three months followed by a recovery period of three months was performed on relevant animals—cynomolgus monkeys. Three dosage levels were used in the experiment. Scheme for the experimental groups is shown in Table 3 below.

TABLE 3

Scheme for evaluation of toxicity in case of multiple subcutaneous administrations

| Group no. | Animal qty | Preparation | Method of administration | Dose |
|---|---|---|---|---|
| 1 | 3 (♂) 3 (♀) | Anti-PD1 monoclonal antibody | intravenous | 5.0 mg/kg |
| 2 | 3 (♂) 3 (♀) | Anti-PD1 monoclonal antibody | | 30.0 mg/kg |
| 3 | 3 (♂)* 3 (♀)* 3 (♂) 3 (♀) | Anti-PD1 monoclonal antibody | | 70.0 mg/kg |
| 4 | 3 (♂) 3 (♀) | Placebo | | — |

The following parameters were evaluated during the study:

results of clinical examinations;

animal weight (before administration and on weeks 1, 3, 5, 7, 9, 11, 13 thereafter);

body temperature (before administration and then weekly until termination of the experiment);

effect on cardiovascular system based on bioelectric activity of heart evaluated by Poly-Spectrum cardiograph; evaluation was performed before administration and then on week 5, 9, 13, 18, 22, 26 of the experiment;

urinalysis (before administration and on week 1, 3, 5, 7, 9, 11, 13 of the experiment);

complete blood analysis on the following parameters: number of erythrocytes, number of leukocytes, hemoglobin concentration, number of lymphocytes, number of monocytes, number of neutrophils, number of eosinophils, number of basophils, number of platelets (before administration, and then once a week starting from the first week of the experiment);

evaluation of effect on blood coagulation system on the following parameters:

activated partial thromboplastin time, fibrinogen concentration, prothrombin time (before administration, then once in two weeks for the period of administration, starting from the second week of the experiment, for the recovery period on week 15, 20 and 25 of the experiment);

biochemical analysis of serum on the following parameters: sodium, potassium, creatinine, urea, alkaline phosphatase, lactate dehydrogenase, total bilirubin, total protein, glucose, triglycerides, aspartate aminotransferase, alanine aminotransferase, total cholesterol (before administration and on week 4, 8, 12, 15, 20 of the experiment);

at the end of the period of administration, animals of satellite group 3* were euthanized, followed by pathomorphological examination thereof; at the end of the study, animals of group 3 and control group were euthanized, followed by pathomorphological examination thereof;

as part of the toxicity study, local irritant effects of preparations were also evaluated, and soft tissues located near the injection areas were therefore selected and histologically examined.

Example 22

Evaluation of Immunotoxicity of Anti-PD1 Antibody Preparation

Examination of immunotoxicity in case of multiple subcutaneous administrations for three months followed by a recovery period for three months was performed on relevant animals—cynomolgus monkeys. Three dosage levels were used in the experiment. The scheme for the experimental groups is shown in Table 4 below.

TABLE 4

Scheme for evaluation of immunotoxicity in case of multiple subcutaneous administrations

| Group no. | Animal Qty | Preparation | Method of administration | Dose |
|---|---|---|---|---|
| 1 | 3 (♂) 3 (♀) | Anti-PD-1 monoclonal antibody | intravenous | 5.0 mg/kg |
| 2 | 3 (♂) 3 (♀) | Anti-PD-1 monoclonal antibody | | 30.0 mg/kg |
| 3 | 3 (♂) 3 (♀) | Anti-PD-1 monoclonal antibody | | 70.0 mg/kg |
| 4 | 3 (♂) 3 (♀) | Placebo | | — |

The following parameters were evaluated during the study:

subpopulation composition of lymphocytes which was evaluated before preparation administration and then on week 3, 7, 13, 21 and 26 of the experiment;

ratio of immunoglobulin classes were evaluated before administration and on week 4, 8, 12, 20, 25 of the experiment;

effect on phagocytosis was evaluated before administration and on week 3, 7, 13, 21, 26 of the experiment;

reaction of blast-transformation of lymphocytes was measured before administration of preparation and then on week 5, 13, 21, 26 of the experiment.

Example 23

Evaluation of Pharmacokinetics and Immunogenicity in Case of Multiple Subcutaneous administrations of anti-PD-1 Antibodies Examination of pharmacokinetics and immunotoxicity in case of multiple subcutaneous administrations for three months, followed by a recovery period for three months was performed on relevant animals—cynomolgus monkeys. Three dosage levels were used in the experiment. Scheme for the experimental groups is shown in Table 5 below.

TABLE 5

Scheme for evaluation of toxicity in case of multiple subcutaneous administrations

| Group no. | Animal qty | Preparation | Method of administration | Dose |
|---|---|---|---|---|
| 1 | 3 (♂) 3 (♀) | Anti-PD-1 monoclonal antibody | intravenous | 5.0 mg/kg |
| 2 | 3 (♂) 3 (♀) | Anti-PD-1 monoclonal antibody | | 30.0 mg/kg |
| 3 | 3 (♂) 3 (♀) | Anti-PD-1 monoclonal antibody | | 70.0 mg/kg |

To evaluate dynamics of preparation concentration and to subsequently calculate pharmacokinetic parameters, blood serum of animals was taken before administration of preparation and then on day 1, 2, 8, 9, 15, 16, 22, 23, 29, 30, 36, 37, 43, 44, 50, 51, 57, 58, 64, 65, 71, 72, 78, 79, 85, 86, 92, 99, 106, 113, 120, 127, 134, 148, 162, 176 of the experiment.

Immunogenicity was evaluated by the level of binding antibodies, and for this purpose, blood was taken and serum was separated before administration of preparation and then on week 4, 8, 12, 20, 26 of the experiment.

The invention claimed is:

1. An antibody, having the ability to bind to a human PD-1 receptor, comprising:
   a heavy chain variable domain that comprises H-CDR1, H-CDR2, H-CDR3 sequences, wherein H-CDR1 comprises an amino acid sequence corresponding to SEQ ID NO: 1, H-CDR2 comprises an amino acid sequence corresponding to SEQ ID NO: 2 and H-CDR3 comprises an amino acid sequence corresponding to SEQ ID NO: 3;
   a light chain variable domain that comprises L-CDR1, L-CDR2, L-CDR3 sequences, wherein L-CDR1 comprises an amino acid sequence corresponding to SEQ ID NO: 4, L-CDR2 comprises an amino acid sequence corresponding to SEQ ID NO: 5 and L-CDR3 comprises an amino acid sequence corresponding to SEQ ID NO: 6.

2. The antibody according to claim 1, characterized in that the antibody contains:
   the heavy chain variable domain comprising an amino acid sequence corresponding to SEQ ID NO:7, and
   the light chain variable domain comprising an amino acid sequence corresponding to SEQ ID NO:8.

3. The antibody according to claim 1, characterized in that the antibody is one of the following human isotypes: IgG1, IgG2, IgG3 and IgG4.

4. The antibody according to claim 1, which binds to human PD-1 and has a heavy chain sequence that corresponds to SEQ ID NO 9.

5. The antibody according to claim 1, which binds to human PD-1 and has a light chain sequence that corresponds to SEQ ID NO 10.

6. A method for preparing the antibody according to claim 1, comprising: producing a host cell comprising a nucleic acid molecule encoding the antibody according to claim 1, culturing the host cell under conditions sufficient to produce the antibody, and isolating and purifying the obtained antibody.

7. A pharmaceutical composition comprising the antibody according to claim 1, in combination with one or more pharmaceutically acceptable excipients, diluents or vehicles.

8. A method of inhibiting the biological activity of PD-1 in a subject in need of such inhibition, comprising administering an effective amount of the antibody according to claim 1.

9. A method for treating a PD-1 mediated oncological and immuno-oncological disease in a patient in need of such treatment, which comprises administering the antibody according to claim 1.

10. The antibody according to claim 1, characterized in that the heavy chain variable domain comprises the amino acid sequence of SEQ ID NO: 7.

11. The antibody according to claim 1, wherein an Fc constant portion comprises one or more mutations at respectively one or more of the positions 228, 233, 234 and 235 in the Fc constant portion that reduce or abolish any of effector functions ADCC, ADCP or CDC, as compared to the natural sequence.

12. An isolated nucleic acid encoding the antibody as defined in claim 1.

13. An expression vector comprising the isolated nucleic acid molecule according to claim 12.

14. A host cell comprising the nucleic acid molecule according to claim 12.

15. A method for producing a host cell, comprising transfecting a suitable stem cell with an expression vector as defined in claim 13.

16. A method for treating a PD-1 mediated oncological and immuno-oncological disease in a patient in need of such treatment, comprising administering the pharmaceutical composition according to claim 7.

* * * * *